US008682042B1

(12) United States Patent
Manion et al.

(10) Patent No.: US 8,682,042 B1
(45) Date of Patent: Mar. 25, 2014

(54) SYSTEM AND METHOD FOR RECEPTION, ANALYSIS, AND ANNOTATION OF PRESCRIPTION DATA

(75) Inventors: Kevin J. Manion, Gibsonia, PA (US); Maria P. Robinson, Wexford, PA (US); R. Michael McGrady, Baden, PA (US)

(73) Assignee: Automated Technologies, Inc., Chesterbrook, PA (US)

( * ) Notice: Subject to any disclaimer, the term of this patent is extended or adjusted under 35 U.S.C. 154(b) by 1642 days.

(21) Appl. No.: 11/705,918

(22) Filed: Feb. 13, 2007

Related U.S. Application Data

(63) Continuation-in-part of application No. 11/107,962, filed on Apr. 15, 2005, now Pat. No. 7,847,970.

(60) Provisional application No. 60/774,359, filed on Feb. 17, 2006, provisional application No. 60/562,797, filed on Apr. 16, 2004.

(51) Int. Cl.
*G06K 9/00* (2006.01)
*G06F 17/00* (2006.01)
*G09G 5/00* (2006.01)
*G06Q 10/00* (2012.01)

(52) U.S. Cl.
USPC ........... 382/128; 382/165; 382/186; 382/187; 382/321; 702/2; 702/3

(58) Field of Classification Search
USPC ................... 382/165, 186, 187, 321; 705/2, 3
See application file for complete search history.

(56) References Cited

U.S. PATENT DOCUMENTS

| | | | | |
|---|---|---|---|---|
| 5,597,995 A * | 1/1997 | Williams et al. | ............... | 235/375 |
| 5,845,255 A * | 12/1998 | Mayaud | ............................ | 705/3 |
| 6,202,923 B1 * | 3/2001 | Boyer et al. | .................. | 235/375 |
| 7,046,848 B1 * | 5/2006 | Olcott | ........................... | 382/176 |
| 2003/0225595 A1 * | 12/2003 | Helmus et al. | ..................... | 705/2 |
| 2004/0019794 A1 * | 1/2004 | Moradi et al. | ................ | 713/185 |
| 2004/0230536 A1 * | 11/2004 | Fung et al. | ...................... | 705/64 |
| 2006/0001690 A1 * | 1/2006 | Martinez et al. | ................ | 347/19 |

* cited by examiner

*Primary Examiner* — Kim Vu
*Assistant Examiner* — Michael Vanchy, Jr.
(74) *Attorney, Agent, or Firm* — Walker & Jocke; Ralph E. Jocke; Daniel D. Wasil

(57) ABSTRACT

A medication order processing system (10) includes a plurality of nursing stations (12, 14, 16). Physician orders prescribing medications for patients are faxed from the nursing stations to a computer which is included in an interchange fax station (28) located at the pharmacy. The interchange fax station is operative to prioritize the orders and to present them to pharmacists working at pharmacist work stations (40, 42). Pharmacist work stations are enabled to review, electronically annotate, and input orders reviewed at the pharmacy work station into a pharmacy order system of the facility. Input to the pharmacy order system results in the medication being administered to the patient. Data related to each patient to which a medication order pertains is captured from screen outputs from the pharmacy order system. The captured data is analyzed to produce data that is stored in a database of the medication order system in correlated relation with image data corresponding to images of medication orders.

34 Claims, 23 Drawing Sheets

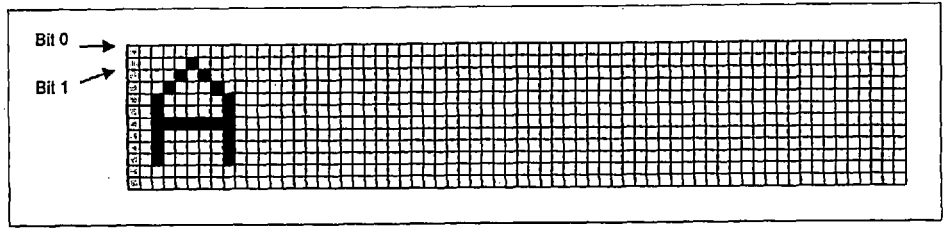
FIG 26
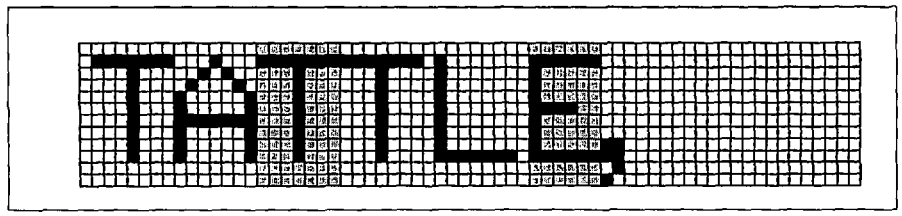
FIG 27
The letter T is:
HEX FFD = 111111111101
HEX FFD = 111111111101
HEX FFD = 111111111101
HEX C01 = 110000000001
HEX FFD = 111111111101
HEX FFD = 111111111101
HEX FFD = 111111111101
FIG 28
The letter M is:
HEX E07 = 111000000111
HEX FF7 = 111111110111
HEX FF7 = 111111110111
HEX E0F = 111000001111
HEX FF7 = 111111110111
HEX FF7 = 111111110111
HEX E0F = 111000001111
FIG 29

XML Schema

This is an example XML file. There are two main sections, one to describe zones and the second to define the fonts used at each zone. There is no practical limit to the number of zones and fonts that can be defined.

Also note that the characters are sorted in ascending order base on the bit patterns that define each character. This is used by the WinScrape application later to optimize the character lookup process.

```xml
<?xml version="1.0"?>
<Interchange>
  <WindowTitle value="Pharmacy Patient System" />
  <Zones>
    <Zone name="PatientName">
      <item name="FontName" value="Arial"/>
      <item name="Left" value="173"/>
      <item name="Top" value="121"/>
      <item name="Width" value="100"/>
      <item name="Height" value="12"/>
      <item name="MustContain" value="" />
      <item name="CannotContain" value="" />
    </Zone>
    <!-- more zones... -->
  </Zones>
  <Fonts>
    <Font name="Arial">
      <item name="DarkTextOnLight" value="True"/>
      <item name="GrayThreshold" value="131"/>
      <item name="MinColsPerSpace" value="5" />
      <item name="HasSerifs" value="False" />
      <item name="SerifPatTop" value="0" hexValue="0000000000000000" />
      <item name="SerifPatBot" value="0" hexValue="0000000000000000" />
      <item name="SerifPatBoth" value="0" hexValue="0000000000000000" />
      <char value="i" index="0" >
          <bitpat index="0" value="3589" hexValue="0000000000000E05" />
      </char>
      <char value="m" index="1" >
          <bitpat index="0" value="3591" hexValue="0000000000000E07" />
          <bitpat index="1" value="4087" hexValue="0000000000000FF7" />
          <bitpat index="2" value="4087" hexValue="0000000000000FF7" />
          <bitpat index="3" value="3599" hexValue="0000000000000E0F" />
          <bitpat index="4" value="4087" hexValue="0000000000000FF7" />
          <bitpat index="5" value="4087" hexValue="0000000000000FF7" />
          <bitpat index="6" value="3599" hexValue="0000000000000E0F" />
      </char>
      <!-- more characters and bit patterns... -->
    </Font>
    <!-- more fonts... -->
  </Fonts>
</Interchange>
```

FIG 30

SYSTEM AND METHOD FOR RECEPTION, ANALYSIS, AND ANNOTATION OF PRESCRIPTION DATA

CROSS REFERENCE TO RELATED APPLICATION

This application also claims benefit pursuant to 35 U.S.C. §119(e) of U.S. Provisional Application Ser. No. 60/774,359 filed Feb. 17, 2006. This application also claims benefit pursuant to 35 U.S.C. §120 of U.S. application Ser. No. 11/107,962 filed Apr. 15, 2005, which application claims the benefit pursuant to 35 U.S.C. §119(e) of U.S. Provisional Application No. 60/562,797 filed Apr. 16, 2004. The disclosure of each of these prior applications is incorporated herein by reference.

TECHNICAL FIELD

This invention relates to systems for providing medications. Specifically this invention relates to systems and methods that facilitate the processing of physician orders for medications by pharmacists.

BACKGROUND OF THE INVENTION

While physicians prescribe medications for patients, pharmacists have responsibility for preparing the medication for delivery to the patient. Once the pharmacist has prepared the medication it may be administered by a medical professional such as a doctor or a nurse.

In hospitals and other medical facilities one or more pharmacy operations are responsible for reviewing the orders by physicians for medications to be given to patients. The pharmacists then prepare or otherwise make the medication available for administration to the patient.

Such requirements can present considerable challenges for pharmacists. There can be difficulties associated with making sure that physician orders, which may include prescriptions for drug medications, are proper. Further, physician orders may need to be retained so that they can be recovered in the event of future questions or a need to further analyze the patient's condition. Thus, there exists a need for improved pharmacy systems and methods for handling physician medical orders.

DISCLOSURE OF INVENTION

In a large medical facility, such as a hospital, pharmacists can receive physician orders from a plurality of nursing stations within the medical facility. One way in which the pharmacy operation can receive such physician medical orders from the nursing stations is via facsimile (fax) transmission. A physician medical order which requests a particular medication for a patient can be prepared in an area adjacent to a nursing station. The medical order can include and/or other information pertinent to the use of medication by the patient. This information can be presented in a structured format such as on a form. The form can be signed by the prescribing physician.

The medication order can then be faxed from a fax machine or otherwise scanned and the image sent via computer at the nursing station to a fax machine or computer in the pharmacy, where the medication orders can be reviewed by a pharmacist. The pharmacist can analyze the information on a physician medical order and, if no issues or concerns are noted, then the pharmacist can have the physician medical order information entered into the pharmacy system or other entry system. Such entry can cause the records associated with the patient to indicate that the medication is to be administered to the patient. This entry can cause an electronic medication order for the patient to be established as one or more database records in the hospital's pharmacy system. The electronic medication order may indicate the medication as well as the dosage, frequency, method of administration, and other information pertinent to providing the medication to the patient. This administration may be done, for example, through a system which provides for the dispensing of medical items from automated dispensers in response to inputs from nurses or other medical professionals in the vicinity of the patient.

In other situations the entry of physician medical order information into the pharmacy system by the pharmacist may cause actions to be taken. These may include, for example, specially preparing the medication for the patient and arranging to have it delivered to the area of a hospital where it is needed.

In some institutional environments medications may be needed immediately, or on a "stat" basis. To handle these orders more rapidly, provision can be made for a separate fax machine or computer in the pharmacy specifically designated for receiving physician orders which have an urgent priority. Physician orders can be sent to this high-priority fax receiving machine or computer by nurses or other medical professionals by dialing the phone number or extension number associated with this stat fax receiving machine rather than the regular fax receiving machine in the pharmacy. Likewise a computer for receiving high priority medication orders will have a particular network address. Orders received through the designated high-priority fax receiving machine or computer for urgent orders can be given priority by the pharmacists entering them into the pharmacy order system or other system.

Pharmacists may sometimes have questions or issues with regard to physician orders that are received. For example, pharmacists may uncover situations where orders are incomplete or inconsistent. This may require the pharmacy to request further information from the doctor or other professional that submitted the order. Pharmacists may communicate to the originating point of the order by return fax or electronic message to try to clarify inconsistencies or to obtain needed information. Such faxed or otherwise requested clarifications may in some cases be requested in writing so as to avoid any misunderstandings.

Pharmacists may also have other issues or concerns regarding received physician orders, such as possible adverse interactions between medications that have already been prescribed for the patient and a newly prescribed medication. In such cases the pharmacists may put the order on "hold" pending the receipt of further clarifying information. Likewise, a pharmacist may determine that a prescribed medication is a duplicate of a medication previously prescribed. Again, in such situations the pharmacist may place the order on hold pending further clarifying information from the originating source. Also, a pharmacist may need to substitute a different brand or type of medication for the one that was prescribed in the order. Again, these issues need to be worked out by the pharmacist before the pharmacist inputs the order into the pharmacy order system, and before the medication is administered to the patient.

In an exemplary embodiment, pharmacists can ensure that all physician orders are properly entered into the pharmacy system and that urgent orders are given appropriate higher priority. In addition, orders that are waiting for further information before they can be entered can be retained so as not to be lost. Further, all such physician orders can be documented. For example, a copy of a fax which resulted in the entry of a medication order can be retained so that it can be later recovered to answer any future questions relevant thereto.

It is an object of an exemplary embodiment to provide an improved system for processing physician orders in a pharmacy.

It is a further object of an exemplary embodiment to provide improved methods for processing physician orders.

Further objects of exemplary embodiments will be made apparent in the following Best Modes for Carrying Out Invention and the appended claims.

The foregoing objects are accomplished in an exemplary embodiment by a system used in a health care facility. The exemplary system includes a plurality of nursing stations. The nursing stations are located in the various wards or other areas of the medical facility where patients are treated. Each nursing station includes a fax machine or other image transfer device for transmitting images of medication orders to a pharmacy.

Communication lines extend between the nursing stations and one or more computers located in the pharmacy. A computer located in the pharmacy is operative to receive the data which comprises faxed or otherwise imaged physician orders that are sent both with normal priority as well as with a high priority.

The computer in the pharmacy that receives the medication orders is in operative connection with one or more pharmacist work stations. The computer which receives the orders is operative to prioritize the incoming orders based on priority and time received, and to present an electronic representation of each order to the pharmacist work stations. Each pharmacist working at a pharmacist work station is automatically presented with the next order in a queue based on time received and priority. In the exemplary embodiment the orders are presented on a screen in a full size visual representation. The pharmacist is also presented with a screen which includes a number of options for functions which can be performed as well as a listing of the pending physician orders in the queue that is waiting to be addressed. In the exemplary embodiment, orders at a top area of the queue have a higher priority than orders at a bottom area of the queue. Of course it should be understood that other queue ordering arrangements may be used.

In the exemplary embodiment the pharmacist work station is operative to automatically locate and enlarge on a first screen a defined quadrant of the order image to more clearly present the patient name and other identifying data to the pharmacist. Upon seeing the patient name and ID number or other data, the pharmacist is enabled to provide inputs to the pharmacist work station which brings up information about the patient on a second screen associated with the pharmacist work station. The pharmacist then may provide an input that causes the defined quadrant to no longer be enlarged. The pharmacist may review the information in the order and take actions such as to enter data corresponding to the order into the pharmacy order system, or place the order on hold for a period of time pending receipt of further information. In some exemplary embodiments the pharmacist may operate the pharmacist work station to place annotations or questions on the order and/or to cause an image of the order to be faxed back or otherwise returned to the originating nursing station with a request for information. Further, in an exemplary embodiment the pharmacist may add additional annotations or markings of a predefined or customized type to the image. This may be stored in a database in correlated relation with the image data corresponding to the order to facilitate accurate record keeping related to the image information.

In the exemplary embodiment the actions of the pharmacist in accessing patient data through the pharmacy system also cause data provided from that system, such as patient name, patient ID, date of birth or other defined data, to be included or correlated with the image data related to the order. Once the pharmacist has completed the entry of the order into the pharmacy order system, the image and the annotations made by the pharmacist are saved in one or more data stores and the electronic representation of the next order is presented to the pharmacist.

It should be understood that these approaches are exemplary and in other embodiments other approaches may be used.

DESCRIPTION OF DRAWINGS

FIG. 8 is an example of an order that has been marked using the various tools for marking the order provided by the pharmacist work station.

FIG. 17 is a substitution order form generated by the exemplary pharmacist workstation.

FIG. 26 is a schematic view representative of how characters are represented and identified in an exemplary embodiment.

FIG. 27 is a further schematic view of characters in a screen output indicating how letters may be represented by digital values.

FIG. 28 is a schematic view showing a set of hexadecimal values corresponding to the letter "t."

FIG. 29 is a set of hexadecimal values corresponding to the letter "m."

FIG. 30 includes descriptive information and a portion of an exemplary schema of an XML document which provides the information which enables interfacing between a pharmacy system and a medication order system.

BEST MODES FOR CARRYING OUT INVENTION

Figure 1:
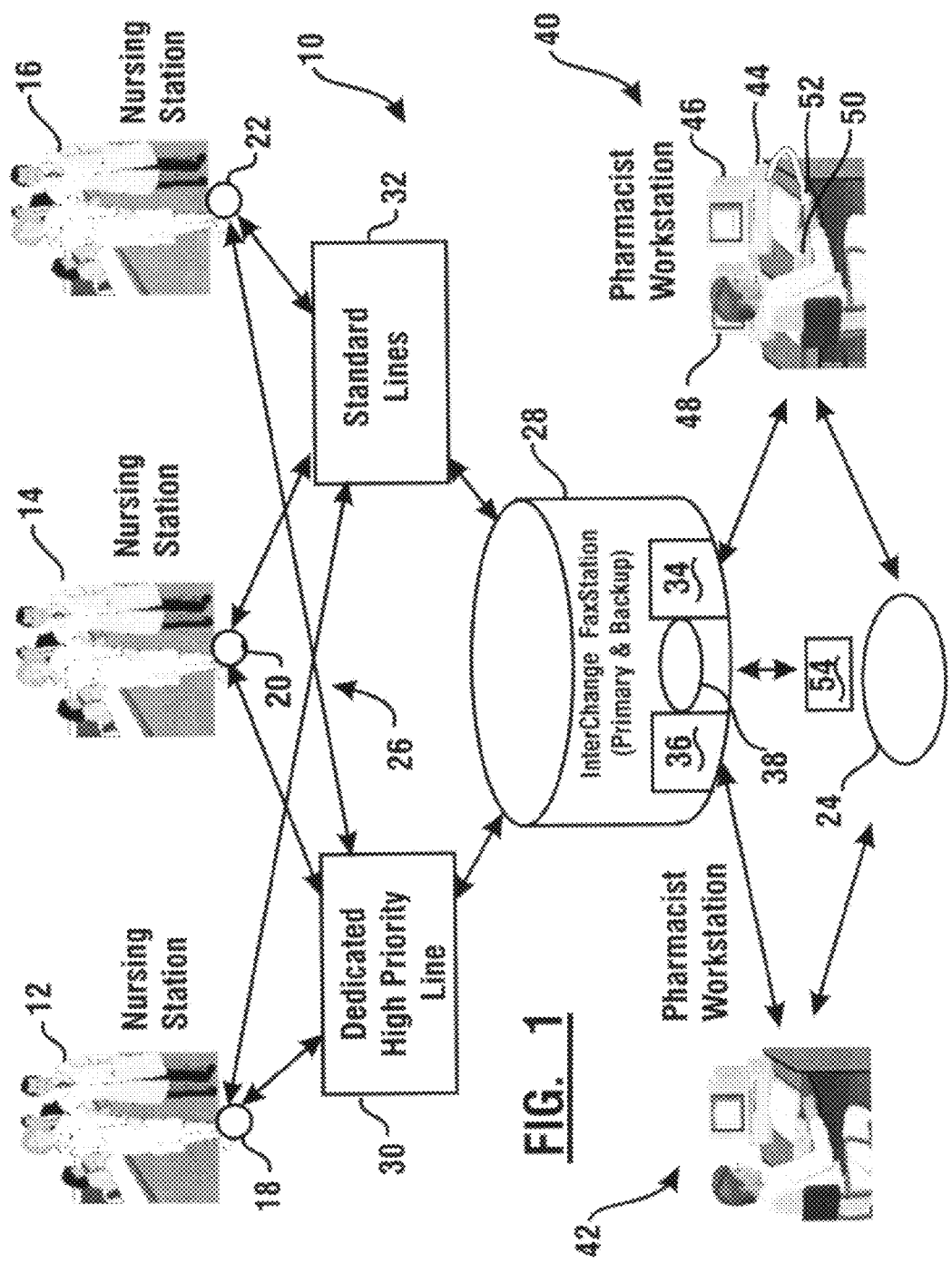
FIG. 1 is a schematic view of a system for processing medication orders.

Referring now to the drawings and particularly to FIG. 1, there is shown therein an exemplary system 10 for processing physician orders for medications to be administered to patients. The exemplary system includes a number of medical stations 12, 14, 16, such as nursing stations. Each nursing station or post is generally located adjacent to wards or rooms where patients may be housed within a hospital or other care facility. Each nursing station generally includes a fax machine or other imaging device 18, 20, 22 which can be used to image a physician order which has been signed or otherwise authorized by a physician and which is to be transmitted to the pharmacy for entry into a pharmacy order system 24 so that the medication can be administered to the patient.

In alternative arrangements, the nursing stations can include computers that can communicate with the pharmacy via Internet transmission or other network communication instead of or in addition to fax transmission communication. A nursing station computer may comprise software enabling input to a medical order form via a keyboard and/or a touch screen. The nursing station computer may also include a signature pad enabling entry of a physician signature on the medical order form therewith. The signed form can then be transmitted to a pharmacy number or a pharmacy network address via fax or the Internet or other network. In some embodiments, a nurse may have a hand-held device which includes a processor that allows completion of an electronic medical order form and input of a physician's signature. Thus, a nurse can fill out a physician medical order and obtain the authorizing physician's signature while away from their nurse's station. Wireless communication can also be used to transmit a physician medical order to a pharmacy. A physician medical order may be transmitted wirelessly from either the nurse's station or the nurse's hand-held device. The nurse's hand-held device may also wirelessly download information therefrom to the nurse's station.

As represented in FIG. 1, a physician medical order transmitting device (e.g., fax machine, computer with a document scanner or other device) at each nursing station is enabled to communicate through phone lines, network or other communication system 26 with one or more computers that are located in the pharmacy. These one or more computers are referred to as an interchange station 28. The interchange station 28 includes one or more processors and data stores suitable for processing and storing instructions and information.

In an exemplary embodiment the interchange station is an interchange fax station. The interchange fax station computers can automate the reception, queuing, and storage of physician medical orders that are received from nursing stations and/or other points within a health care facility. In the exemplary embodiment, fax reception is supported on multiple phone lines. These phone lines include at least one designated line 30 for urgent or "stat" handling as well as at least one line 32 for normal handling. The interchange fax station 28 of the exemplary embodiment is enabled to be in communication with multiple lines for receiving stat orders as well as multiple lines for receiving normal (non urgent) orders. For example, station 28 can comprise a computer station including at least two phone lines, each line assigned a different handling priority. The fax handling priority can be based on which of the two phone lines received the medication order.

The interchange fax station 28 of the exemplary embodiment is operative to receive fax data corresponding to images of physician orders and to automatically place the images in storage in at least one relational database. The images (or data representative of the images) can be placed in the appropriate stat or normal queue based on the fax line on which the fax was received. The interchange fax station, if necessary, is also operative, in accordance with its programming, to conduct image processing on received orders, such as the decoding of received faxes, converting the faxes to compressed electronic image format, and storing the electronic images in the database. The exemplary interchange fax station is also operative to continue to store orders that are entered, processed, or deleted until a configurable time limit is reached. Upon expiration of this time limit they are permanently removed from the database.

Exemplary forms of the interchange fax station may also operate in accordance with their programming to manipulate the data corresponding to order images to improve clarity. This may be accomplished, for example, by changing pixel values for pixels in the images to provide greater contrast between light and dark pixels. Alternatively, image data may be manipulated to be aligned with an imposed coordinate system by the computer to compensate for any skewing of the order as it moved in the fax machine. Other types of image data manipulation may be provided in accordance with the programming of the computer software of the interchange fax station.

In the exemplary embodiment the interchange fax station 28 includes a primary computer 34 and a backup computer 36 that are physically connected via an Ethernet hub 38. The primary computer 34 includes mirrored hot swappable disk drives while the backup computer is generally maintained without drives. This enables the backup computer to be made the primary computer by swapping the disk drives. Thus the backup computer may become the primary computer without touching any network cables or other connections. Further in the exemplary embodiment both the primary and backup computers are connected to a power source through an uninterruptible power supply.

In the exemplary embodiment the interchange fax station 28 is in operative communication with one or more pharmacist work stations 40, 42. The pharmacist work stations 40, 42 comprise computers at which pharmacists can operate to review medication orders. The pharmacy system, in an exemplary embodiment, is operative to enable pharmacists to automate the process of converting physician medication orders on paper into electronic medication orders within the pharmacy system 24. In an exemplary arrangement the work stations are connected via a network (intranet and/or Internet) and allow users thereof to communicate with each other, such as by electronic messages (e-mail, instant messaging, etc.).

In an exemplary embodiment, a pharmacist work station includes a computer 44 with dual output display screens 46, 48, a keyboard 50 and a mouse 52. The pharmacist work station can be operated in accordance with the executable instructions of the computer software therefor. The screens or "monitors" 46, 48 are preferably sized to be able to display electronic representations of physician medication orders at full size. The exemplary pharmacist station includes a single keyboard and mouse that can operate and provide inputs through graphical user interfaces output through both display screens 46, 48 without the need for a switch or other signal directing device. In an exemplary embodiment, one display screen is used by a pharmacist to review physician orders requesting medications and the other display screen is used by the same pharmacist to enter approved medication orders into the pharmacy order system. In other embodiments a pharmacist work station can have more than two display screens.

The exemplary pharmacist work station 40 includes output display screens with touch screen capability. The touch screen may act in a manner similar to a mouse and provide a fast user-friendly way to annotate an electronic representation of a physician order by touching the screen. In the exemplary embodiment the pharmacist work station 40 is also operative to output an audible tone through a speaker or other audio output device to indicate if the screen has been touched.

Further, in the exemplary embodiment, input devices such as the keyboard, touch screen, and/or mouse can be used to add annotations (e.g., notes, checkmarks, highlighting, and other indicators) to the electronic representation of the image. This facilitates the ability of a pharmacist to annotate a displayed image of a physician medication order with pharmacist-added information, such as comments or questions.

Further, in the exemplary embodiment, the pharmacist work station is operative to capture data regarding the patient such as the patient ID, name, date of birth, gender, ward/room location, and/or other information from the pharmacy order entry system and to incorporate that information into displayed image data and in the relational database. This is done in the exemplary embodiment through use of a software "screen scraper" operating in the computer 44 which captures data corresponding to a graphic representation of the information from selected parts of visible outputs provided from the pharmacy order system. For example, a first one of the dual display screens can show patient (identifying) data from the pharmacy order system. This displayed patient data (or a portion thereof) can be captured and then copied into an electronic image of a physician medical order (from the medication order system) displayed on the second of the dual display screens. Capturing this (patient data) information in the medical order image data helps to verify that the order was entered for the appropriate patient. The electronic image of the physician medical order containing the added patient data can then be stored. A work station enables data from a pharmacy order system to be analyzed on one display monitor, captured therefrom, inserted for display (along with a medication order) on a display monitor of a medication order system, and saved in the medication order system. Hence, data can be captured/copied from the pharmacy order system to the medication order system, and vice versa. Of course it should be understood that the pharmacy order system comprises a network including one or more connected computers which operate to include medication orders in the stored data associated with the patient which helps to assure that the medication ordered for the patient by the physician is administered.

In other exemplary embodiments one or more computers of the medication order system may be programmed in a manner hereinafter discussed to automatically capture and interpret data output on a display screen from the pharmacy order system. This may enable data to be transferred from the pharmacy order system to the medication order system based on the screen outputs. This transferred data is enabled to be stored in one or more databases associated with computers of the medication order system, such as the interchange fax station. The captured data may be stored in correlated relation with medication order data and image data. This approach may avoid the need for a pharmacist to manually key in at least some data for storage in a database of the medication order system and may also facilitate searching of data that is stored therein.

In the exemplary embodiment the pharmacist work station 40 is programmed to provide numerous useful functions. These include prioritizing the physician orders so that they are handled in a priority order. In the exemplary embodiment, orders are prioritized based on when they are received as well as whether they have stat or normal priority. When pharmacists first log in to a pharmacist work station and after the handling of each order is completed, or otherwise disposed of by being discarded or placed on hold, the pharmacist work station through interaction with the interchange fax station operates in accordance with its programming to select automatically the next fax physician order that has the highest priority for processing. Of course, as is later apparent, in the exemplary embodiment a pharmacist may optionally select any fax physician order to review by inputs to their pharmacist work station.

In the exemplary embodiment the pharmacist work station 42 may be programmed to operate in connection with the interchange fax station 28 so as to selectively direct particular orders for processing. For example, the system may be configured so that a particular pharmacist may review and process all orders. Alternatively the system may be configured so that certain faxes are assigned to specific pharmacists, or to a separate pharmacy operation within the pharmacy facility. This may be accomplished through programming of the interchange fax station 28 and pharmacist work station. For example, faxes may be directed based on certain criteria such as the fax machine from which the order originated, the communication line that received the fax order, the type/amount of medication requested, the location of the patient, the availability of the pharmacist, or other criteria. In other embodiments the functions of fax station 28 and the functions of a pharmacist work station may be combined to operate as a single integral unit.

In an exemplary embodiment, faxed medication orders can be temporarily placed on "hold" by the pharmacist while waiting for clarification. This can be done by an appropriate input by the pharmacist. The pharmacist work station is programmed so that faxes that have been placed on hold are necessarily defined to time out of the hold state and revert back into the appropriate queue for handling. This helps to assure that a fax will not be forgotten if it is placed in a hold state.

In an exemplary embodiment the programming of the pharmacist work station includes an automatic zoom feature. In an exemplary embodiment this feature automatically zooms in on and enlarges a defined quadrant of the fax image when the image is first displayed on a display screen of the work station. This may be useful with regard to order forms where necessary patient information and ID numbers are needed for purposes of queuing up corresponding information in the pharmacy order system may be small or otherwise difficult to read. Further in an exemplary embodiment fax images are enabled to be selectively zoomed, panned and rotated through inputs to the pharmacist work station. A pharmacist may provide one or more manual inputs through one or more input devices of the pharmacist work station which corresponds to the visual information in the displayed patient order. This may include inputting the patient name or other data input through a keyboard which causes the pharmacy system to output information concerning the patient from a data store in the pharmacy system through a screen of the pharmacist work station.

Further, in alternative embodiments, characters in the selected quadrant may be analyzed by character recognition software operating in a computer to resolve patient name and ID data. This may be done for example, by using character recognition software that is commercially available from Carreker, Parascript or A2iA. Such software may be used to resolve electronically the characters corresponding to the data which corresponds to written data on the medication order. A computer such as the interchange fax station or the pharmacist work station can provide at least one input, such as a message that includes at least some of this resolved data to the pharmacy system as an input which automatically causes the pharmacy data corresponding to the patient to be output. In such embodiments the pharmacist need only verify the accuracy of the analysis by reviewing the outputs on the screens rather than providing manual inputs to bring up the patient data from the pharmacy system.

In the exemplary embodiment the pharmacist work station has included in its programming certain electronic image annotation tools. These annotation tools include the ability to provide checkmarks, highlighting, electronic ink, notes and stamps to allow the pharmacist to annotate the electronic image as they perform their work.

In an exemplary embodiment the pharmacist work station 40 in conjunction with the interchange fax station 28 is programmed to provide a fax-back function. The fax-back function allows pharmacists to quickly return a fax to the sending nursing station (or other location) for clarification. For example, human-readable (typed or written or predefined) comments or questions added to a physician medication order at a pharmacy can be faxed-back to a nursing station for reading by a nurse. Alternatively faxes may be sent by the pharmacist through inputs to their work station to another fax machine such as a machine located in a physician's office. This enables the pharmacist to receive the clarifying information necessary to enter the order more rapidly and in a documented manner.

The exemplary pharmacist work station 40 further provides therapeutic substitution capability. This feature enables the pharmacist to quickly choose a predefined substitute medication or medication property or aspect, such as the form, dose or strength. Such predefined therapeutic substitutions may be set by hospital policy through predefined tables and rules which are stored in connection with the pharmacist work station.

Further features of the exemplary embodiment of the pharmacist work station include security features. These features may include, for example, user ID card or combined card and PIN access to assure that the pharmacist work station can only be accessed by an authorized user. Further, exemplary embodiments impose a periodic mandatory PIN change to minimize the risk that a pharmacist's personal login information may be stolen by unauthorized persons. A further aspect of an exemplary embodiment provides for a user to be automatically logged out of the terminal if they do not provide inputs within a preset time. This avoids the risk that a user will leave a terminal in an unattended condition such that it can be accessed by unauthorized persons.

The exemplary embodiments also provide an audit trail of information that has been input to the system. In addition, because the interchange fax station captures patient information directly from the pharmacy order system and stores it in correlated relation with the corresponding medication order from the physician, the order data can be searched and analyzed using the information that is derived from the pharmacy order system. This facilitates recovering information that is stored in the system. Of course these approaches are exemplary and in other embodiments other or additional features may be included.

In an exemplary embodiment, reviewer work stations 54 may be provided. Reviewer work stations 54 may be similar to pharmacist work stations 40 except with more limited functionality. In an exemplary embodiment, medication orders cannot be entered into the pharmacy order system through reviewer work stations 54. However, the stations 54 can enable a user to review electronic representations of faxes and annotations regarding physician orders represented by data stored in the interchange fax station computers and/or in other data stores. The exemplary reviewer work stations 54 also provide the ability to change the priority status of physician medication orders. For example, a reviewer work station can be used to raise the status of a particular physician order from normal to stat. The exemplary reviewer work stations 54 also provide the ability to annotate an electronic image of a physician medication order. For example, a reviewer work station can be used by an assistant to annotate a new order to indicate that a first level of review was completed and by whom. If an obvious error was noted in the review then the order can be faxed back to the originating medical station along with annotation questions to resolve the error. A first level of review can reduce pharmacist review time. Also, a reviewer work station can be used to further annotate a previously annotated physician medication order.

In an exemplary embodiment the interchange reviewer work station 54 may be configured to review all orders or selected orders within the pharmacy. For example, a reviewer work station may be configured to review orders that are being handled in a particular pharmacy location. Alternatively reviewer work stations may be configured to monitor orders which are coming from particular nursing stations, fax or other imaging machines or groups of devices, either inside or outside the facility. This enables a reviewer to monitor various types of information as appropriate to carry out their functions.

In the exemplary embodiment the interchange reviewer work station 54 may also be operative responsive to user inputs to zoom, pan, and rotate fax images. Further a reviewer at a reviewer work station 54 can provide markings such as checkmarks, highlighting, electronic ink, notes, and stamps so that they can annotate images as they wish. In addition the reviewer work stations in the exemplary embodiment are enabled to conduct searches based on data that has been stored in image data and that was captured from the pharmacy order system. The reviewer work stations 54 may also include security features and audit capabilities similar to those provided for pharmacist work stations. Of course these approaches are exemplary and in other embodiments reviewer stations may be provided which have different or other types of functions. Furthermore, pharmacist work stations and reviewer work stations may be located in satellite offices which are part of the pharmacy or pharmacy arrangement. As previously discussed, work stations (i.e., pharmacist and reviewer work stations) can be connected to the same network (e.g., intranet and/or Internet) allowing the pharmacy arrangement to have work stations remotely located relative to each other. For example, one or more pharmacists may be situated in the pharmacy arrangement at a geographic location that is remotely disposed from the reviewers' geographic location.

Figure 2:
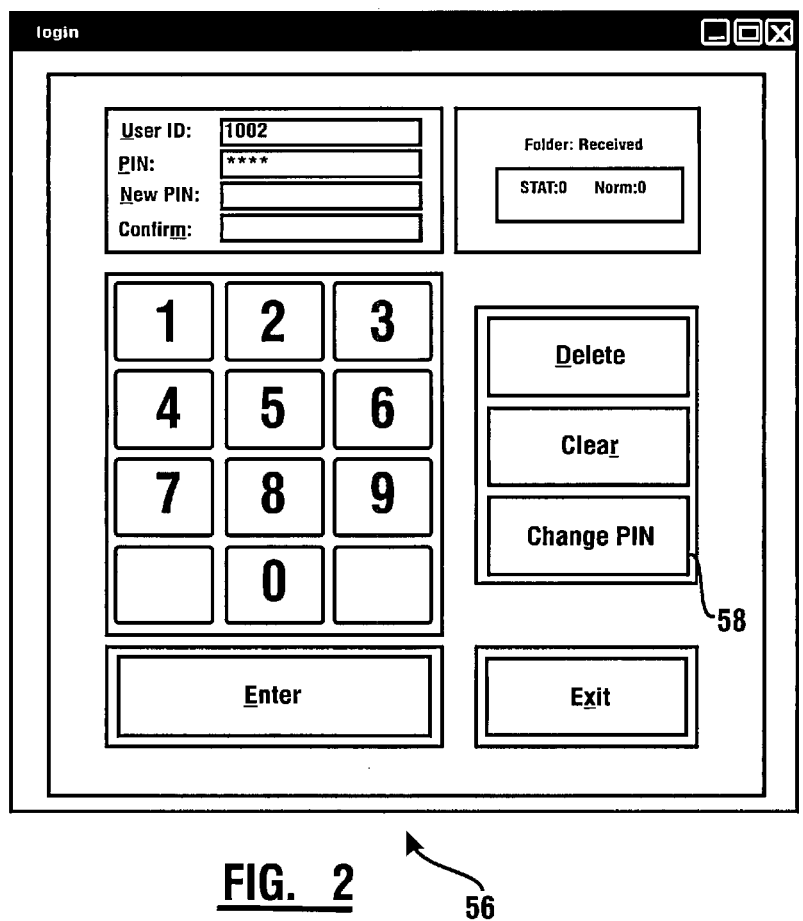
FIG. 2 is an exemplary login screen at the pharmacist work station.

FIG. 2 shows an exemplary embodiment of a login screen 56 that is produced by the pharmacist work station. A pharmacist is required to provide information through inputs responsive to this screen before being able to access the functions available through the pharmacist terminal. Further as previously discussed, reviewer work stations 54 may also incorporate similar features. In the exemplary embodiment, a pharmacist is required to provide both a user ID and PIN in order to gain access to the system. Of course as previously discussed, in some embodiments the user may be required to provide data which is included on a card which is read by a card reader or similar device that is in operative connection with the pharmacy terminal. As indicated in FIG. 2 an icon 58 is provided for a user to change their PIN. If a user selects this option after entering the correct PIN they may input a substitute PIN. The substitute PIN may be used by them thereafter for purposes of accessing the system. In some exemplary embodiments the pharmacist work station is programmed so that the user is required to change their PIN periodically within a set number of days. If the user fails to make such a change in a timely manner they may be prompted through an output from the work station after logging in to do so and prevented from accessing further functions until a PIN change is input. Of course these approaches are exemplary.

Figure 3:
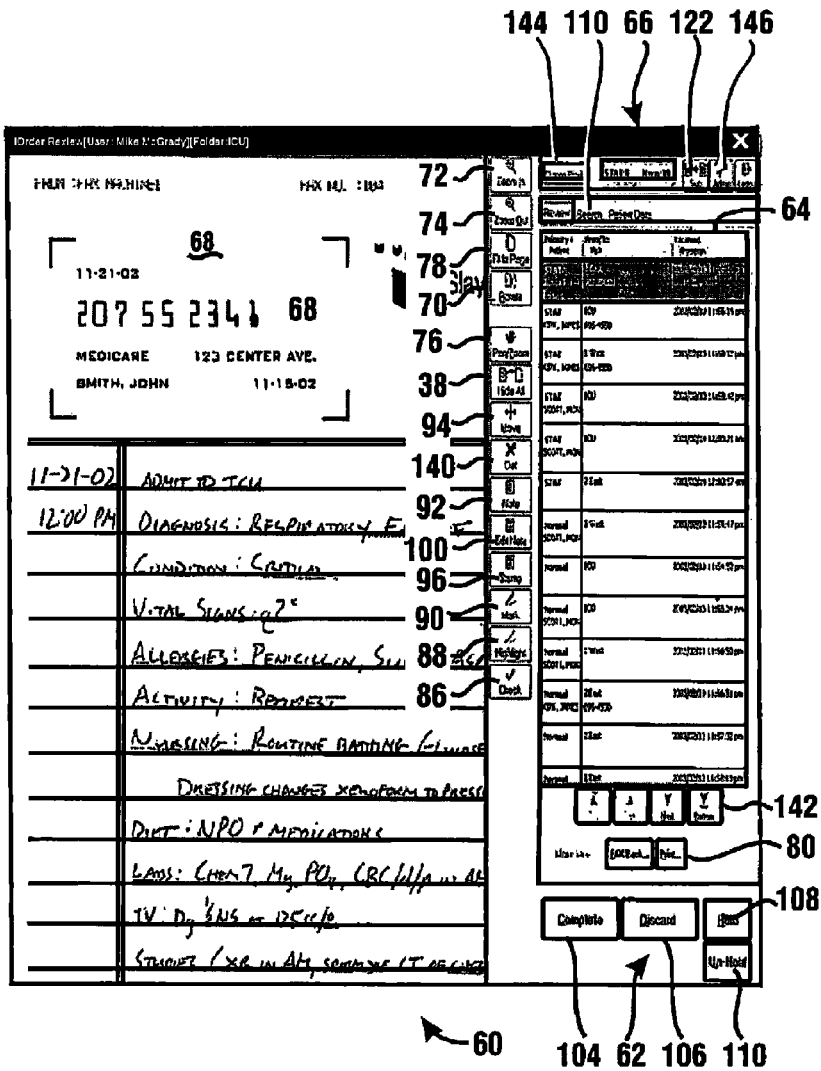
FIG. 3 is an exemplary view of a medication order presented on a screen of a pharmacist work station.

In an exemplary embodiment, once a pharmacist has logged into the pharmacist work station successfully, the pharmacist is presented through a display screen an order review browser interface 60 shown in FIG. 3. As discussed in more detail later, a review button 120 may be used to place the display screen back in the format shown in FIG. 3. The format of the exemplary physician order review interface screen shown in FIG. 3 includes the displaying of at least a portion of an electronic image corresponding to a received physician medical order. Through the order review interface 60, a pharmacist is able to browse through and review electronic images corresponding to the physician orders. Controls that are accessible through the order review interface 60 enable the pharmacist to rotate, zoom in or out, scroll, and pan the electronic representation of the faxed physician order. The controls also enable the pharmacist to place annotations, such as markings and/or comments, on the electronic representation of the faxed physician order. These controls can be displayed on the screen, which can have touch screen capability. As previously discussed, work station input devices such as a keyboard, touch screen, and/or mouse can be used to add annotations to an electronic representation of a displayed image. After the pharmacist has reviewed the order it may be indicated as completed, discarded, or placed on hold through the selection of window buttons 62 shown in the order review interface screen.

The format of the exemplary physician order review interface 60 shown in FIG. 3 also includes the displaying of a queue 64 of physician orders in priority ordering or sequencing in a window. Physician orders are automatically ordered in the queue, first by stat priority and then by normal priority based on their time received. Stat orders are ordered in first-in first-out priority order. Likewise, normal orders are ordered in first-in first-out priority order. As shown in FIG. 3, the stat physician orders are prioritized higher in the queue than the normal physician orders. The stat physician orders are arranged by time relative to each other. Likewise, the normal physician orders are arranged by time relative to each other.

The physician orders queue window can indicate the highest priority fax order at the top of the queue. In an exemplary embodiment, when the pharmacist logs on to a pharmacist work station and the work station mode is set to display the queue window, the top priority fax image is automatically selected and displayed on the display screen through operation of the interchange fax station, the pharmacist work station, and the pharmacist work station display device. A work station enables a pharmacist the ability to simultaneously display on the same display screen both a physician medication order along with an order-prioritizing queue containing other awaiting orders. The display of the order queue enables a pharmacist to be aware of a change in medication order filling priorities. For example, assuming there are no stat orders pending, if a stat order then comes in while the pharmacist is reviewing a non-stat order, the work station enables the pharmacist to note the stat order in the queue, stop reviewing the currently displayed (lower priority) non-stat order, handle the stat order, and then return to complete the previously displayed non-stat order. In other arrangements the work station can notify the pharmacist (whether or not the queue is displayed) of a new stat order via a pop-up notification window on the display screen, an audible alarm, a visible alarm (e.g., flashing light), and/or some other notification method.

As represented in FIG. 3 on the right side of the order review interface screen, the queue 64 of pending physician orders is displayed. This area of the output indicates the orders in the queue, and the order being displayed is highlighted. Further as shown in the upper right of the order review interface window, an output indicator 66 is provided to the user showing the numeric number of stat orders and normal orders currently in the queue.

In exemplary embodiments, when the pharmacist logs onto the pharmacist work station the electronic image corresponding to top priority fax 68 is automatically selected and displayed on the left-hand side of a display screen. Further, in exemplary embodiments, the pharmacist work station is programmed to automatically zoom to a selected specific quadrant of the order image and enlarge it on the screen. The pharmacist may choose to process the order that is displayed or may choose to handle another fax from the queue. This is done by highlighting that fax in the listing of orders in the queue 64 presented on the right side of the display. In exemplary embodiments, when multiple pharmacists' work stations are being used, physician orders that have been processed by other pharmacists are displayed in a distinctive color. Once another pharmacist has begun to process the physician order, a pharmacist at the pharmacist work station can review these orders in a read-only mode. The pharmacist work station is programmed so that toolbar options and icons that would otherwise be operative in the user interface when another pharmacist at another work station is handling a particular order, are grayed out and are unable to be selected when the pharmacist is reviewing the order.

In the exemplary embodiment the data in the order queue shown in the order review interface 60 may be sorted by the criteria in the column headings. For example, orders may be displayed by priority from where they originated or from the received physician. By clicking (e.g., via a mouse or keyboard keys) on a column heading the display of the queue orders is automatically reordered. In addition, the data may be selected by either ascending or descending order. The queue priority currently imposed on a display screen is reflected in an exemplary embodiment by the presentation of a plus sign (+) for ascending order or a minus sign (−) for descending order in the column for the criteria which is being used to order the data.

In exemplary embodiments, the area to the right of the physician order 68 shown in FIG. 3 includes icons for tools and controls that can be used by the pharmacist. These tools and controls allow the pharmacist to manipulate or modify the displayed electronic image and to annotate directly in the electronic image.

In the exemplary embodiment a rotate icon 70 is provided. Icons are alternatively referred to herein as buttons. Selection/activation of a displayed rotate icon 70 by clicking on the screen (e.g., via a mouse or keyboard), using voice command, or touching the touch screen at the icon can rotate the physician order image 90 degrees. For example, if the fax is received upside down, clicking the rotate button 70 twice will cause the fax to be displayed right side up.

A zoom in icon 72 is provided. When the zoom in button 72 is selected, the point where the mouse indicator resides on the order image becomes the center of a zoom area. Holding the mouse button on the spot will continue to cause the effect of zooming in on the electronic image until the mouse button is released.

Similarly, a zoom out icon 74 is provided. Selection of the zoom out button 74 makes the image smaller. The point where the mouse is clicked on the image becomes the center of a zoom out area. Holding the mouse button on the spot continues the zoom out effect until the mouse button is released.

In an exemplary embodiment a pan/zoom icon 76 is provided to move the image within the image window. When the pan/zoom button 76 is selected, holding the mouse button down and moving the mouse is operative to cause the image to move. Holding the mouse button down without moving the mouse causes the image to be zoomed in around the spot where the mouse pointer is located. In the exemplary embodiment, after using the rotate, zoom, and pan controls, the image may be restored to full size by touching the fit-to-page button 78. This causes the image to be displayed in full size and in normal perspective within the area of the display screen.

The exemplary embodiment of the pharmacist work station also provides the pharmacist with printing options. In some operations pharmacists will wish to print every fax or in other operations only selected faxes will be printed. In addition, in some situations pharmacists may wish to have faxes printed with all electronic annotations they have included on (added to) the fax image, while in other situations only the original fax as received (or the fax image as originally stored, without annotations) is desired.

Figure 4:
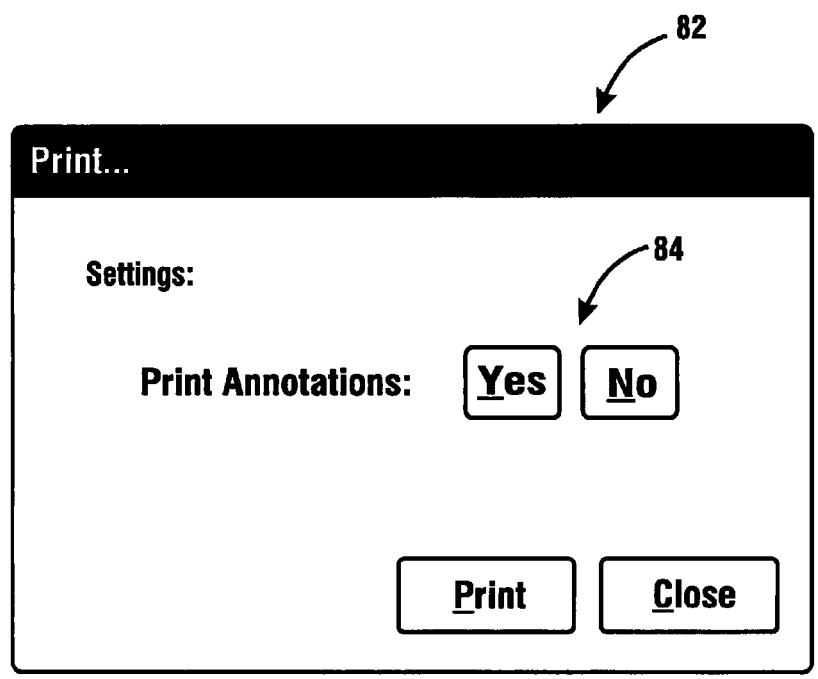
FIG. 4 is an exemplary print window output on a pharmacist work station.

In an exemplary embodiment, the order review interface screen (FIG. 3) includes a print button 80. Selecting the print button causes the print window 82 shown in FIG. 4 to be displayed. The print window 82 has buttons 84 which enable the user to select whether to print the electronic representation of the physician order with or without annotations. Further if the pharmacist has initially chosen to print a physician order but then changes their mind, they may simply choose to close the print window. Of course, as previously discussed, these approaches are exemplary and in some embodiments every order may be printed either with or without annotations based on the programming of the pharmacist terminal, whether the pharmacist chooses to specifically print the order or not.

Figure 5:
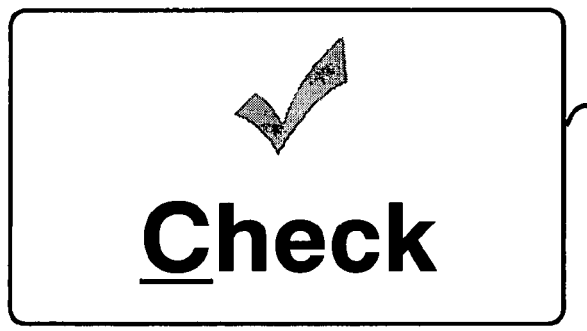
FIG. 5 is an exemplary icon associated with a check tool provided by the pharmacist work station.

In the exemplary embodiment the pharmacist work station enables the pharmacist to utilize electronic image annotation tools which can be used to provide electronic markings in the image data associated with a physician order. As shown in FIG. 3, the order review interface screen includes a check tool icon 86. This icon is shown in further detail in FIG. 5. Clicking on or using the touch screen to select the check tool icon 86 will cause a virtual check mark to appear in the electronic representation of the fax image each time thereafter that the screen is touched until another tool is selected. Checkmarks are shown in the physician order image in FIG. 8.

Figure 6:
FIG. 6 is an exemplary icon associated with a highlight tool provided by the pharmacist work station.

A highlight tool icon 88 is also available in the order review interface screen, as shown in FIG. 3. The highlight tool icon is shown in more detail in FIG. 6. Selecting the highlight tool icon 88 enables highlighting of portions of a displayed electronic image of a physician order with a virtual color marker. This may be done by a user, such as a pharmacist, moving their finger over the image if there is a touch screen or through use of a mouse. The highlighting function will continue (remain active) in the exemplary embodiment until another tool is selected.

Figure 7:
FIG. 7 is an exemplary icon associated with a marking tool provided through an exemplary pharmacist work station.

The exemplary embodiment also includes a mark tool icon 90 as represented in FIG. 3, and which is shown in more detail in FIG. 7. Selecting the mark tool icon 90 enables a user to virtually write or draw on the electronic representation of a displayed physician order. This enables a user to virtually circle particular portions of text or otherwise provide markings represented on the displayed image either through the mouse or by use of the touch screen. Once the marking tool is selected, touching the screen or moving the mouse will result in further markings appearing on the displayed image until another tool is selected.

Figure 8:
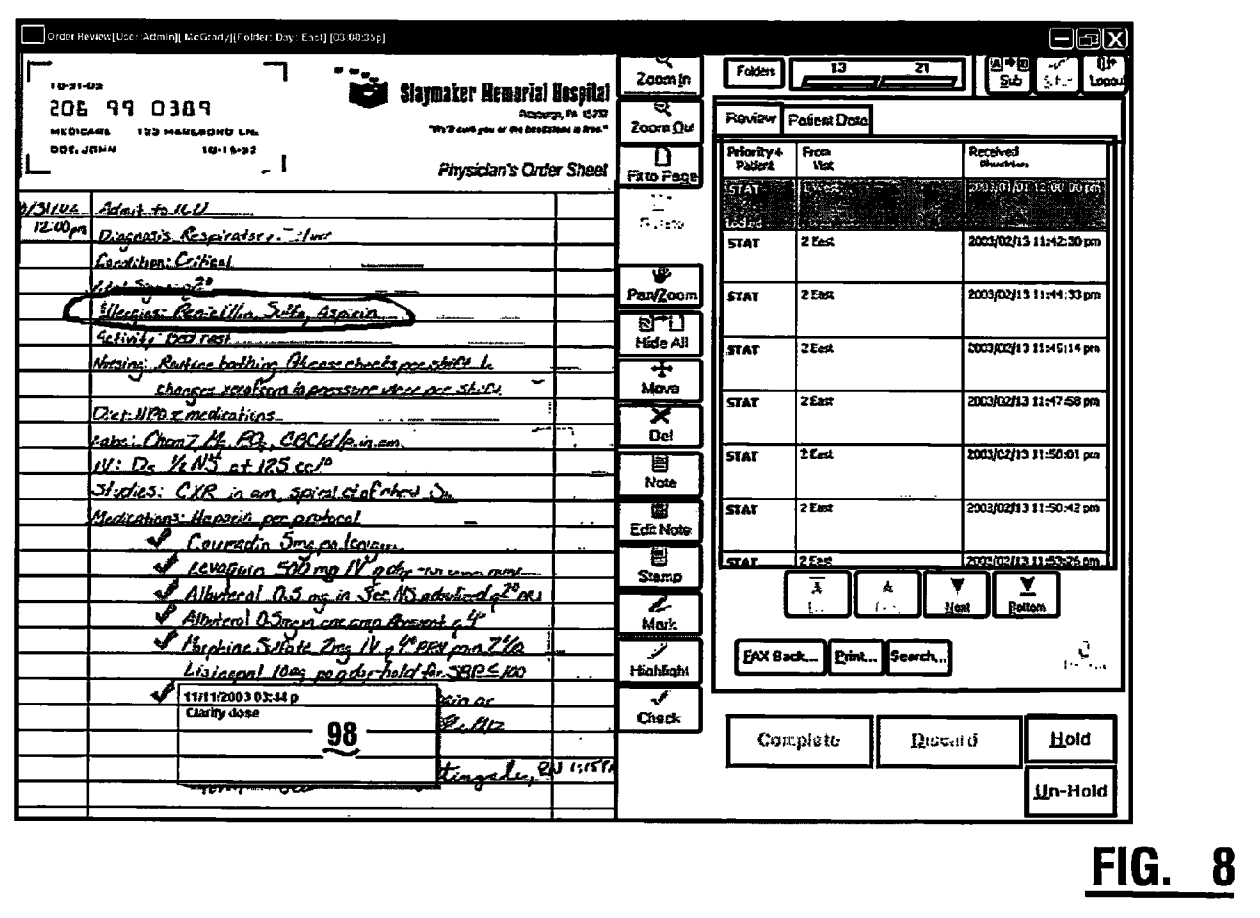

FIG. 8 shows an example of a physician order image that has been marked with checkmarks and a marking tool. As can be seen, the marking tool was used to circle a particular item in the imaged physician order. These virtual markings in the exemplary embodiment are represented by data in a database associated with the order image. These virtual markings can be stored in accordance with the programming of the computer to become a permanent integrated part of the physician order image data or to be separable therefrom. The approach taken will depend on system configuration. An annotated physician medical order including a comment can be stored in a single file. Alternatively, annotated physician medical order including a comment can be stored in plural associated files. For example, a comment can be separately stored in a file that is in correlated relationship with a file containing the originally received physician medical order. A pharmacist at a work station has the option of displaying an image of the annotated physician medical order or only the image of the originally received physician medical order. Each dated annotation can be stored as a separate file that can be layered over preceding annotation layers during display of the annotated order. A pharmacist is able to backtrack to view changes in an annotation history of a physician medical order. Of course these approaches are exemplary, and other storage methods enabling the viewing of annotation history can be used.

Figure 9:
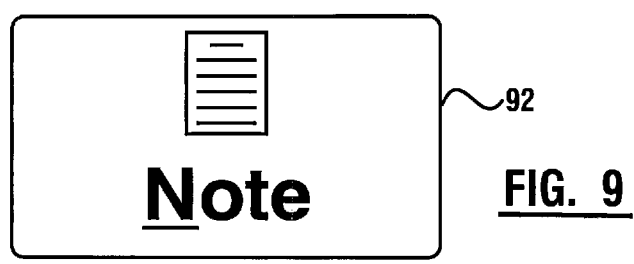
FIG. 9 is an icon associated with a note tool provided by the exemplary pharmacist work station.

A further feature of the exemplary embodiment is a note tool. This is represented in FIG. 3 and the note tool icon 92 which is shown in more detail in FIG. 9. The note tool icon 92 enables a user to enter or place a note in the image at a desired location. Selecting the note tool icon 92 and then touching or clicking (e.g., with a mouse or key) on a screen location place (or affixes) the note on the image at that specific image location. A note comprises a note area. The work station enables a user to define the size and/or shape of the default note area. Thus, a default note having a predefined area can be attached to an image at a particular image location.

In the exemplary embodiment the note is automatically stamped so as to include the date and time of the note. Furthermore, pressing a right arrow key on the keyboard 50 enables the pharmacist to include text within the note area. The text added to the note may be text typed by the pharmacist, or text already predefined and retrieved from a data store, or text written using a previously discussed marking tool (associated with mark tool icon 90). After text entry into the note is finished, pressing the enter key on the keyboard completes the note.

Figure 12:
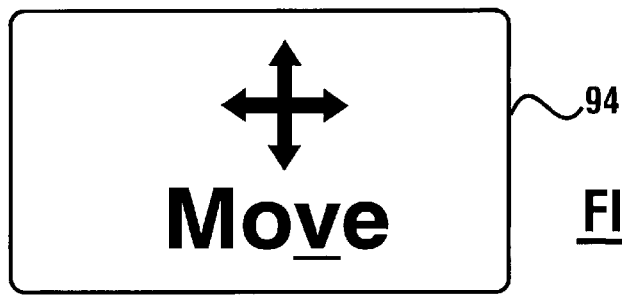
FIG. 12 is an icon associated with a move tool.

Further, a move icon 94 which is shown in FIG. 3 and which is also shown in greater detail in FIG. 12, can be selected to enable a user to move an inserted note so as to reposition the note in the image once it has been applied. This is done by selecting the move icon 94 and then touching the touch screen or moving the mouse to a desired screen location and clicking. This will cause the note to be imposed at that location in the order image.

Figure 10:
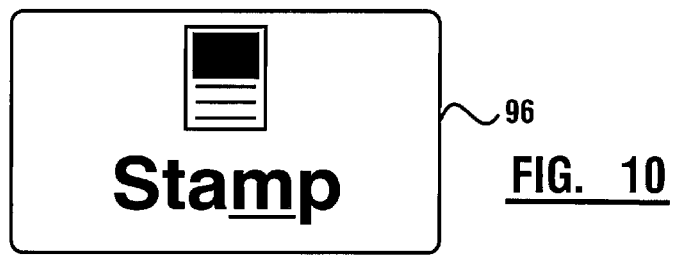
FIG. 10 is an icon associated with a stamp tool.
Figure 11:
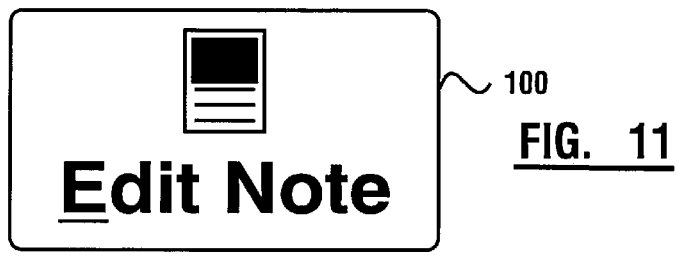
FIG. 11 is an icon associated with an edit tool.

The exemplary embodiment also includes a stamp icon 96 represented in FIG. 3 and shown in more detail in FIG. 10. The exemplary stamp tool is a special version of the note tool. The stamp tool enables use of a user-defined library of predefined messages or comments that are automatically placed in a note without any required typing. That is, a note already containing predefined text can be accessed for insertion. Predefined notes can be selected so that a user does not have to add (e.g., type) the text into a note area. Selecting stamp icon 96 causes a window to appear which includes a drop-down list of predefined notes. A particular note is selected by providing an input using the mouse or touchscreen. Thereafter, touching or clicking on the order image places the note with its predefined text in the indicated location on the image. In addition, the move icon 94 shown in FIG. 12 can be selected for purposes of moving a predefined stamp. FIG. 8 shows an exemplary form of a predefined note or stamp 98 attached to or placed on an image of a physician medical order. In exemplary embodiments, notes and stamps may be placed in overlying relation in the image, and later separated as desired by selecting the move icon 94 and function.

A further function provided through the exemplary order interface screen shown in FIG. 3 is an edit note function. The edit note icon 100 may be selected by a user to enable the pharmacist to modify the text included within a note or stamp. Thus, a pharmacist may supplement text already included in a pharmacist-created note or in a predefined stamp to tailor it to a particular order image. Alternatively, a note previously presented can be modified based on information which a pharmacist receives or discovers which may necessitate a change. The edit note feature also enables a user to modify the size or dimensions of a note area.

Figure 13:
FIG. 13 is an icon associated with the fax back tool.

Another function provided in the exemplary embodiment of the pharmacist work station is the ability to fax back a message to an originating fax machine at a work station or to another location. This function is achieved by selecting the fax back icon 102 shown in FIG. 3 and in more detail in FIG. 13. In the exemplary embodiment, clicking on the fax back icon 102 causes a window to be displayed which includes data representing a list of nursing stations and other locations, from which faxed physician orders have been received. The originating fax station for the particular order being handled in the display is automatically highlighted in the list. A fax transmission button is also presented in the window, and clicking on the window button causes an annotated fax corresponding to the modified or annotated order image to be automatically sent back to the originating fax station. The annotated fax may include the entire original physician medical order (with the annotated markings thereon) or only a portion of the original physician medical order. For example, only the physician medical order page having the annotated marking thereon may be faxed back to the originating nursing station.

Alternatively, the pharmacist is enabled to select a different station to receive the annotated fax by clicking on or touching an alternative station in the list so as to select it. This enables the pharmacist to direct the return fax to another appropriate station such as the requesting physician's office. This feature enables the pharmacist to direct an annotated fax image back to the particular location or person originating it so as to obtain clarification or other information that may be necessary to complete the physician order. In exemplary embodiments, if a pharmacist (or other person authorized to operate a work station) desires, multiple faxes corresponding to the same annotated fax image may be sent to different locations.

A return fax may be received at a nursing station as a printed paper fax via a paper receiving fax machine at the nursing station. A nurse or physician can respond to a pharmacist's question in a received annotated physician medical order paper fax by marking directly on the paper and then transmitting it back to the pharmacy.

It should be understood that a return fax may be transmitted from the pharmacy as an electronic image corresponding to an annotated (or modified) physician medical order. For example, a modified physician medical order can be sent from the pharmacy to the originating nursing station. The nursing station can have a computer and display device capable of receiving and displaying the electronic image. The nursing station computer can have fax receiving and fax sending software. The pharmacy-added markings on the annotated physician medical order can be viewed at a nursing station display screen. A nurse or physician can respond to a pharmacist's question in a received modified or annotated physician medical order by transmitting another fax to the pharmacy. The response (second) fax can be sent electronically from the nursing station to the pharmacy via the nursing station computer using fax sending software. Alternatively, a response message can be first be printed out on paper and then faxed via a paper receiving fax machine to the pharmacy. Similarly, the original fax from the nursing station to the pharmacy can be both sent and received as a paper fax. In an exemplary embodiment the nurse stations (and the pharmacy) are able to transmit and receive both electronic faxes and paper faxes. Also, the electronic faxes may be transmitted and received wirelessly.

As also represented in FIG. 3, the exemplary pharmacist work station includes other function buttons 62 that can be selected responsive to inputs. These function buttons include a complete button 104 which is normally selected by a pharmacist when they have completed placing entry of the physician order data into the pharmacy order system. In an exemplary embodiment, upon completion of an order entry, an annotated physician order image is saved and the next image in the priority ordering is presented.

A discard button 106 is also provided. The discard button 106 can be selected when a pharmacist is required to discard the image. This may be done for numerous reasons. For example, in response to an inquiry from the pharmacist, the physician responsible for the order may request that the order be canceled. Furthermore, the patient to whom the physician medical order was directed may have expired and will not be needing the medication.

A hold button 108 is also provided. The hold function is generally selected when more information on an order is needed. As previously discussed, orders at an upper or top area of the queue have a higher priority than orders at a lower or bottom area of the queue. In the exemplary embodiment, placing an order on hold temporarily moves it to a position at the bottom of the order queue until a time out value is reached. Thereafter it is moved to the top of the order queue to determine if the desired additional information has been received. This feature helps to minimize the risk that a medication order will be lost. The time period assigned to the time out value can be defined and/or adjusted by a work station user. Orders that have been placed on hold can be released manually by selecting an un-hold icon 111. Selecting the un-hold icon 111 will release the order earlier than the timing function.

In the exemplary embodiment, a selection of the complete 104, hold 108, or discard 106 buttons by the pharmacist causes the image to no longer be (currently) displayed at the pharmacist work station, and the next image in the queue that is available for processing is presented in the display. Of course, the data corresponding to the previous image is stored in the database associated with the interchange fax station for archive, later review, and/or further processing. Of course these approaches are exemplary and in other embodiments other approaches may be used.

Figure 14:
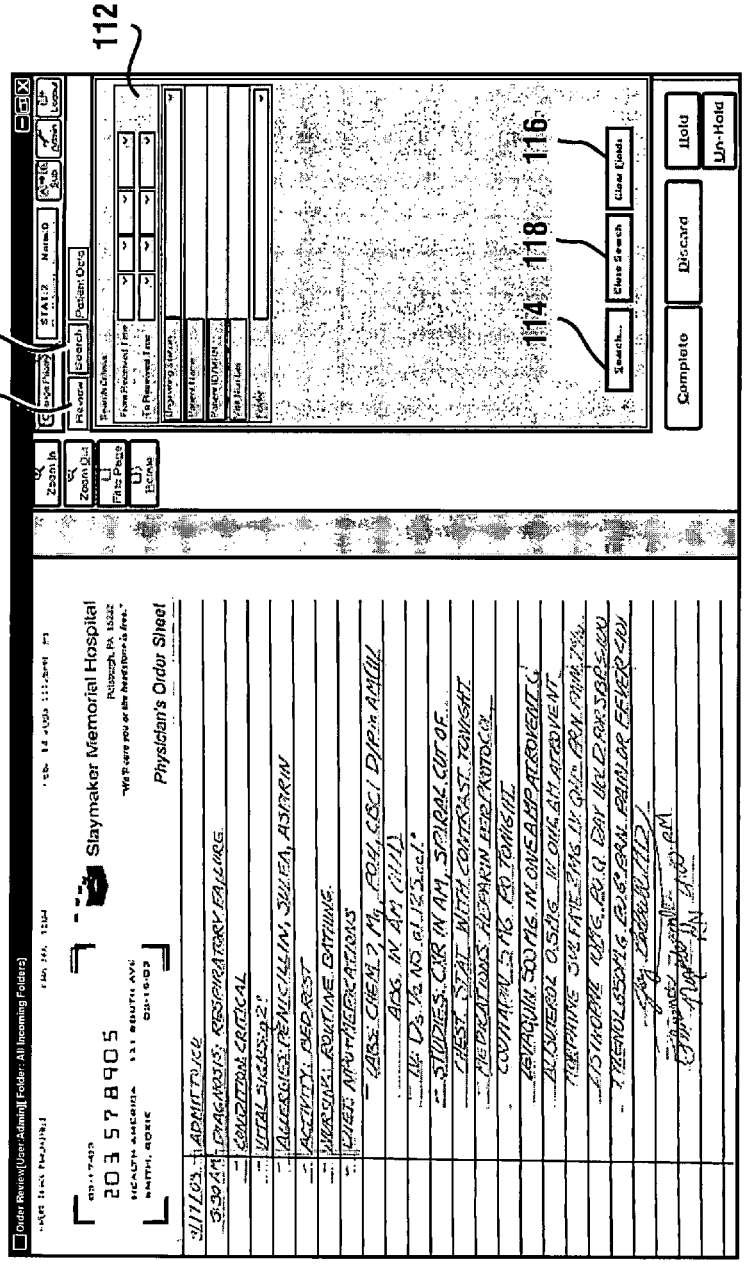
FIG. 14 is an output screen from a pharmacist work station associated with a tool for searching for a particular faxed order.

As further represented in the order review interface screen in FIG. 3, a searching function is provided through the programs executable in the exemplary pharmacist work station. Selecting the search button 110 causes a search folder 112 to be displayed on the right side of the order review interface screen, as shown in FIG. 14. The format of the physician order review interface screen shown in FIG. 14 includes the displaying of a search folder window. Selecting the search function provides a matrix which a user can populate with search criteria. This matrix is shown in greater detail in FIG. 15. By populating the data in this matrix and selecting the lower search icon 114, the user may search for orders that meet the user's selected criteria. The orders that are uncovered in the search are output to the left side of the exemplary output screen. In the exemplary embodiment, a user may conduct multiple searches, and change search data by inputting different criteria and clearing prior criteria. This is done by selecting the clear fields icon 116. The displayed search folder can be closed by actuating a close icon 118 or by selecting the review icon 120, which places the screen back in the display format shown in FIG. 3.

Figure 15:
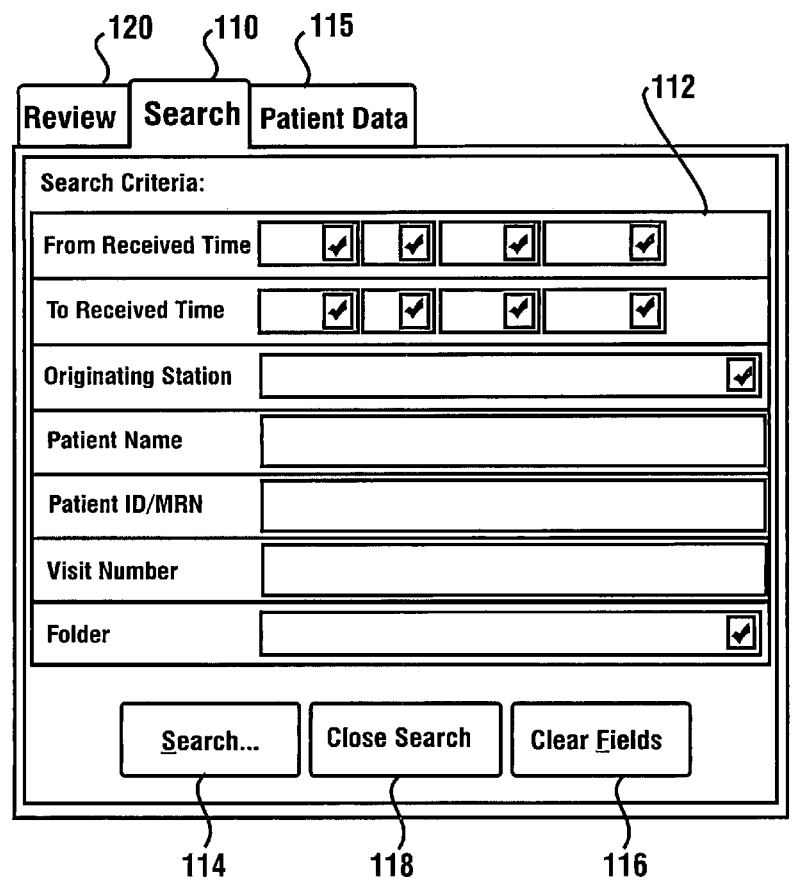
FIG. 15 is an enlarged view of a portion of an output screen which is populated by a pharmacist in order to search for a faxed order.

Another screen format available for display can be selected by using the patient data button 115 shown in FIG. 3, with an enlarged view shown in FIG. 15. Upon using this screen icon, data corresponding to a particular patient is displayed in a patient data window. The particular patient can be the patient corresponding to the currently displayed physician order. Also, the particular patient can be the patient retrieved in a search result. Data from the pharmacy order entry system regarding the patient's name, ID, date of birth, ward, room, and other information can be displayed for review at the pharmacist work station. As previously discussed, besides a patient data window, the pharmacist work station enables the screen display of several other windows, including a queue window and a search folder window.

It should be understood that the positions of the displayed buttons described herein are exemplary. In other exemplary embodiments the buttons may be relocated in a display. For example, FIG. 8 shows a search button located adjacent to the print button. It should also be understood that in other exemplary arrangements additional or fewer buttons may be used. For example, the order review interface screen of FIG. 3 shows an additional close search button. The screen of FIG. 8 shows a refresh button. The refresh button can be used to redisplay the current image. When work stations are connected to the Internet or other similar network, the refresh button can also be used to reload the current web page. In additional exemplary embodiments the workstation operator has the option of selecting which operator buttons are to be displayed.

In an exemplary embodiment, pharmacists are also enabled to achieve therapeutic substitution for medications to be provided to patients. A physician issuing the medication order will write the order listing the medications they want the patient to receive. Generally the pharmacist takes these orders, reviews them and if there are no issues, inputs the data to the pharmacy order system to create a medication order for the patient. These medication orders result in the medication being provided to the patient through the operation of the hospitals' medication delivery systems.

However, in some cases the hospital by policy allows for medications to be substituted. This process may be referred to as therapeutic substitution which may be a medication substitution or changing an aspect of the prescription as originally written before entry into the pharmacy system. An example may be substituting one brand name medication for another or substituting a generic. Alternatively a substitution may include changing the dose, route or frequency of the particular medication. In some exemplary embodiments even though a pharmacist may be able to make the therapeutic substitution according to preapproved substitution policies, a new physician order must be created and signed by the pharmacist to document the substitution. Alternatively the identification system used to identify the pharmacist who operates the pharmacist terminal may be used to automatically input into the record the pharmacist's name.

In the exemplary embodiment, if the pharmacist inputs the substitute order and the physician does not agree, the physician will create a new medication order to discontinue the substitution and select a new medication.

Figure 16:
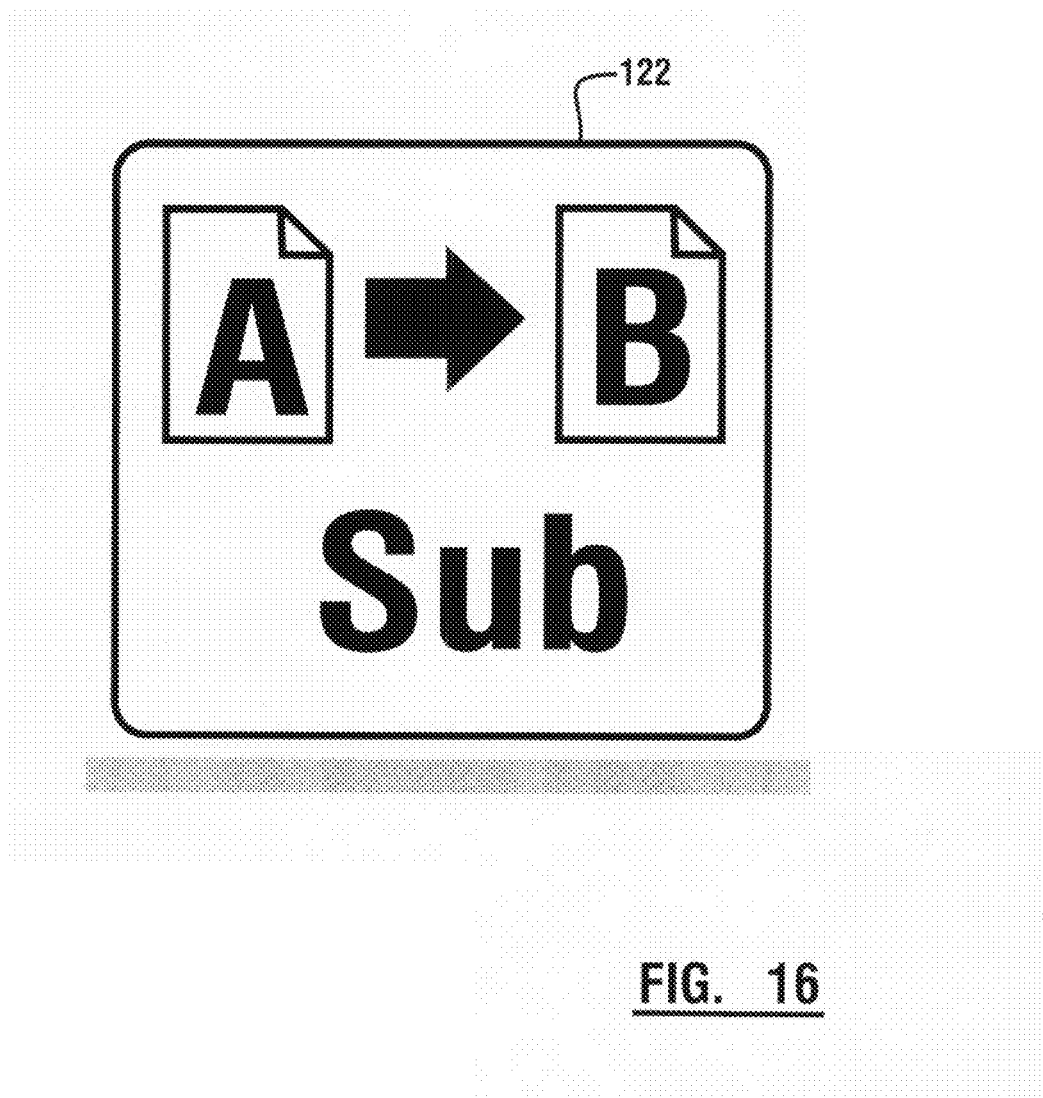
FIG. 16 is an icon associated with a substitution function provided the pharmacist workstation.
Figure 17:
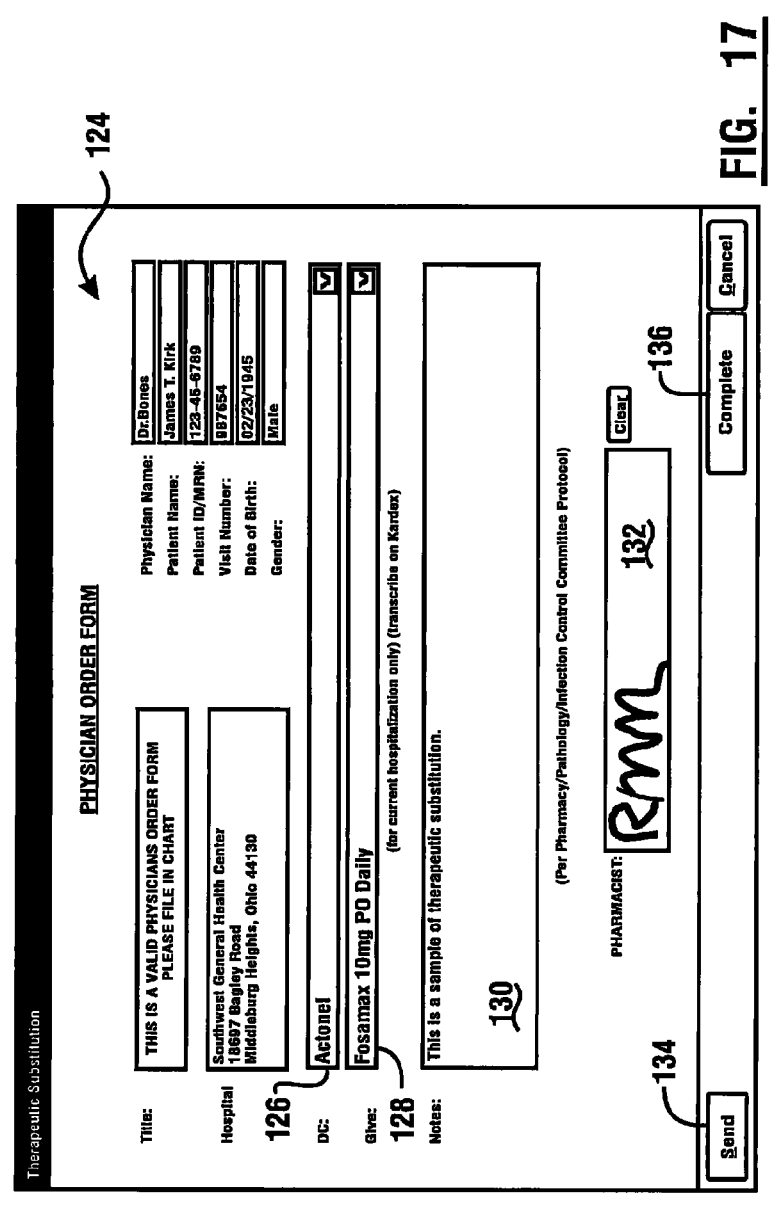

In the exemplary embodiment a pharmacist is enabled to accomplish a therapeutic substitution order by selecting the substitution order icon 122 shown in FIG. 3 and in additional detail in FIG. 16. Selecting the substitution order icon causes the physician order form 124 shown in FIG. 17 to be presented. In this form the pharmacist is enabled to select the physician ordered medication from a drop-down list 126 indicated DC. The pharmacist is also enabled to select the medication, dose, route and frequency to be substituted from a drop-down list 128 selectable in the "give" field. In the exemplary embodiment a predefined note associated with the medication that is being substituted is automatically placed in a note area 130 in the form. Additional information may be added to the note by the pharmacist clicking into the note and typing. Further as represented in FIG. 17 the pharmacist may sign the order in a signature area 132 with virtual electronic ink using the mark tool function. The originating nursing station from which the original order was presented is selected by the pharmacist work station by default to receive the completed physician order form. By clicking on or activating (e.g., via a mouse or keyboard or touch or voice command) the displayed send button 134 the pharmacist is enabled to send a fax of the therapeutic substitution form to the originating station. Further by clicking on the complete button 136 the substitution order is stored to the database. Of course these approaches are exemplary, in other embodiments other approaches may be used.

In an exemplary embodiment additional functions may be provided. For example, as shown in FIG. 3 a hide icon 138 is provided. The hide icon may be selected to review the order image without overlying markings. Selecting the icon again causes the markings to be restored.

A further exemplary function is the delete function which is selected using a delete icon 140. The delete icon may be selected, and then touching or clicking on a previously applied pharmacist marking, will cause the marking to be deleted. Such functions may be useful for correcting mistakes. It may also be useful for eliminating notes that particular information is needed once the information is received. In some exemplary embodiments the computer may be operative to store markings that were made and then deleted for purposes of providing a complete record of order processing. Of course, these approaches are exemplary.

The exemplary user interface screen also includes arrow icons 142 that can be used to scroll through the physician medical orders waiting in the queue 64. For example, arrows representative of top of queue, previous page, next page, and bottom of queue can be used, as shown in FIG. 3. A change priority icon 144 is also provided. The change priority icon can be used to change the status of a particular selected order form the normal category to the stat category, and vice versa.

Of course these functions and interfaces are exemplary and in other embodiments other or different functions may be provided.

Further, in the exemplary embodiment, a plurality of hot keys are provided to facilitate the rapid operation of the pharmacist work station by a pharmacist. These hot keys are basically a combination of keyboard inputs that enable the pharmacist to select the various functions without having to utilize the touch screen or mouse interface. The exemplary embodiment enables a pharmacist to become familiar with these hot key combinations so as to facilitate selecting desired functions without the normal selection activities. In some embodiments these hot keys may be predefined for the system. Alternatively, embodiments may be devised so that a pharmacist can establish their own hot key approaches to meet their particular preferences. Of course these approaches are exemplary of many approaches that may be used in various embodiments.

Exemplary embodiments of the system may include a capability for an administrator to set certain parameters associated with the operation of the interchange fax station and pharmacist work stations. These may include, for example, setting work station settings, setting up user accounts, establishing hardware configurations, setting up folder configurations, providing the information for therapeutic substitutions, setting up notes and stamp configurations and predefining stamp language. Of course these administrative functions are exemplary and in other embodiments other approaches may be used. In the exemplary embodiment, administrator functions are accessed by actuating an administrator icon 146. Selecting this icon enables the user access to those administrative functions they have been authorized to access based on the setup of the work station.

Figure 18:
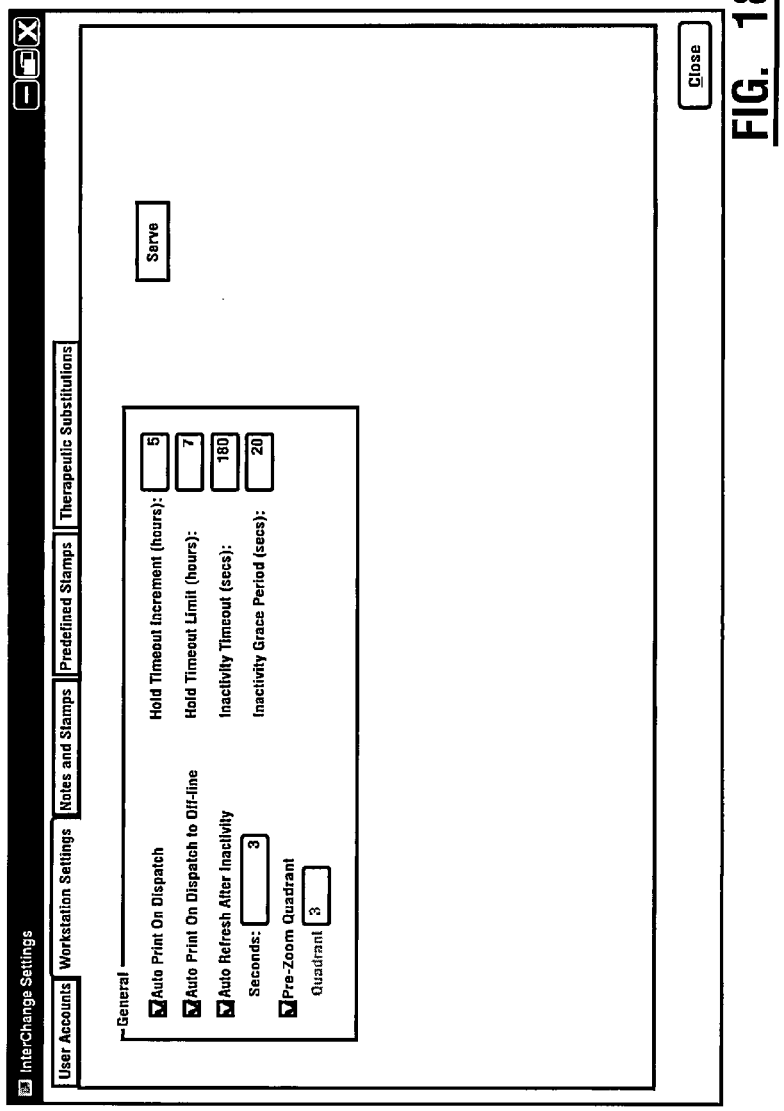
FIG. 18 is an exemplary screen output by a pharmacist workstation to access administration functions.

FIG. 18 shows an exemplary output screen from the pharmacist work station which is used in an exemplary embodiment to set work station settings. One option which is selectable from this screen is an autoprint on dispatch feature. When checked responsive to a user input the autoprint on dispatch feature executes programmed logic in the pharmacist work station to cause every image and/or annotation to be printed on a default printer.

Another option in the exemplary embodiment is an autoprint on dispatch to offline feature. This feature when selected sends every image dispatched to the offline folder and its annotations to the default printer. The offline folder is a special feature that allows the pharmacist to fulfill order requests while the pharmacy order system may be unavailable. This may occur due to malfunctions or other problems with the pharmacy order system.

Another feature in the exemplary embodiment is an auto-refresh feature. When checked responsive to a user input it refreshes the pharmacist work station at a rate that is specified through the input number of seconds indicated on the work station settings screen.

Another option configurable in the exemplary embodiment is a pre-zoom quadrant. When checked responsive to a user input, the electronic representation of a fax physician order will be first presented to the pharmacist zoomed-in on the specified quadrant. As previously discussed, this may be useful for reading the patient's name and user ID or medical record number (MRN) for entry into the pharmacy order system. In the exemplary embodiment the user is enabled to specify or select through an input provided through a drop-down menu, the quadrant which is to be initially zoomed. Quadrant one is the upper left area of the physician order image. Quadrant two is upper right. Quadrant three is lower left and Quadrant 4 is lower right. A quadrant can be enlarged to encompass the entire display screen area. The selected quadrant can be the default quadrant until changed. As previously discussed, the pre-zoom quadrant feature can be set by the user so that the first image displayed on the display screen is the default-selected zoomed quadrant. Thus, an enlargement of a preselected image location or defined image area can be the initial or default screens automatically displayed when the physician order image is first selected for display. It should be understood that in other embodiments other areas of a screen may be specified for purposes of providing automatic zooming, abstraction, or maximization depending on the programming of the pharmacist work station. For example, the borders of a quadrant can be user-defined by using drawing tools to electronically describe or outline the desired quadrant area on the display screen. Thus, a new quadrant, such as one overlapping areas of quadrant one and quadrant 2, can be created, saved, and used again.

Another option in the exemplary embodiment of the work station settings shown in FIG. 18 is the hold timeout increment. The hold timeout increment specifies in hours the amount of time to keep a physician order on hold each time that the hold button is selected. The hold timeout increment is the standard time that will be provided when a hold is first specified. As previously discussed, a time period assigned to the time out value can be selected by a work station user.

Another option of the exemplary embodiment is a hold timeout limit, which corresponds to the maximum number of hours that the system will allow an order to be placed on hold. Thus, for example, if a pharmacist has to place an order on hold multiple times, once the hold timeout limit is reached, the order will rise to the top of the queue and cannot be placed on hold again. A time period assigned to the hold timeout limit can be selected or defined by a work station user. A hold timeout limit can be adjusted to encompass or correspond to cumulative time out values. For example, a time out value and a hold timeout limit can each be set relative to each other to ensure that a fixed number (e.g., three) of holds can be placed on an order. Once the set number of holds on an order has expired, no more hold for that order is permitted.

It should be understood that the maximum time that an order can be placed on hold may expire while the current hold timeout increment (timeout value) has not yet expired. When the hold timeout limit is set as having priority over any hold timeout increment, then the order will be placed near the top of the queue. In other embodiments, the hold timeout increment and hold timeout limit can be set relative to each other so that a current hold timeout increment will continue until its expiration regardless of the hold timeout limit expiration. However, because of the hold timeout limit expiration, no more holds on that order are allowed to begin.

It should also be understood that a non-urgent order released from hold may be positioned adjacent to or near the top of the queue, instead of at the very top of the queue. The queue can be set up so that urgent orders always stay at a (reserved) top portion of the queue. Thus, a non-urgent order released from hold can be moved from the bottom area of the queue to the top area of the queue directly below any urgent orders. In other embodiments, an order identified or labeled as urgent cannot be placed on hold.

In an exemplary embodiment, an out-of-hold time notification can be made available to the operator of the work station when the maximum time limit has been reached. For example, the order represented in the display queue may be flagged with a particular mark or different color indicative of being out of hold time. Likewise, an out-of-hold time notification or warning can be immediately displayed on the display screen (or an audible signal activated) when the hold button is selected and there is no more hold time remaining.

A further option is the inactivity timeout. The inactivity timeout specifies the amount of time in seconds that a user's session remains active without any keyboard or mouse activity. When this time interval expires, the pharmacist work station will wait the additional number of seconds specified in the indicated inactivity grace period field. After the grace period expires the user is automatically logged off the system. This feature is useful in an exemplary embodiment to assure that pharmacist work stations are not left unattended for extended periods of time in which unauthorized persons can gain access to the system and the associated confidential information contained therein. Of course these pharmacist work stations configurable settings are exemplary and in other embodiments other configurations may be used.

Another administration function which can be set for one or more pharmacist work stations by an administrator is user account information. This can be accessed by an authorized administrator by selecting the user accounts administrator folder tab from the administrator menu. Such a selection is represented by the screen output shown in FIG. 19. From the user accounts window an administrator is enabled to add, modify or delete user accounts and assign access rights for particular pharmacist or other users. In the exemplary embodiment the pharmacist work station is programmed so that the administrator can also disable a user account temporarily such as when a user is on vacation.

Figure 19:
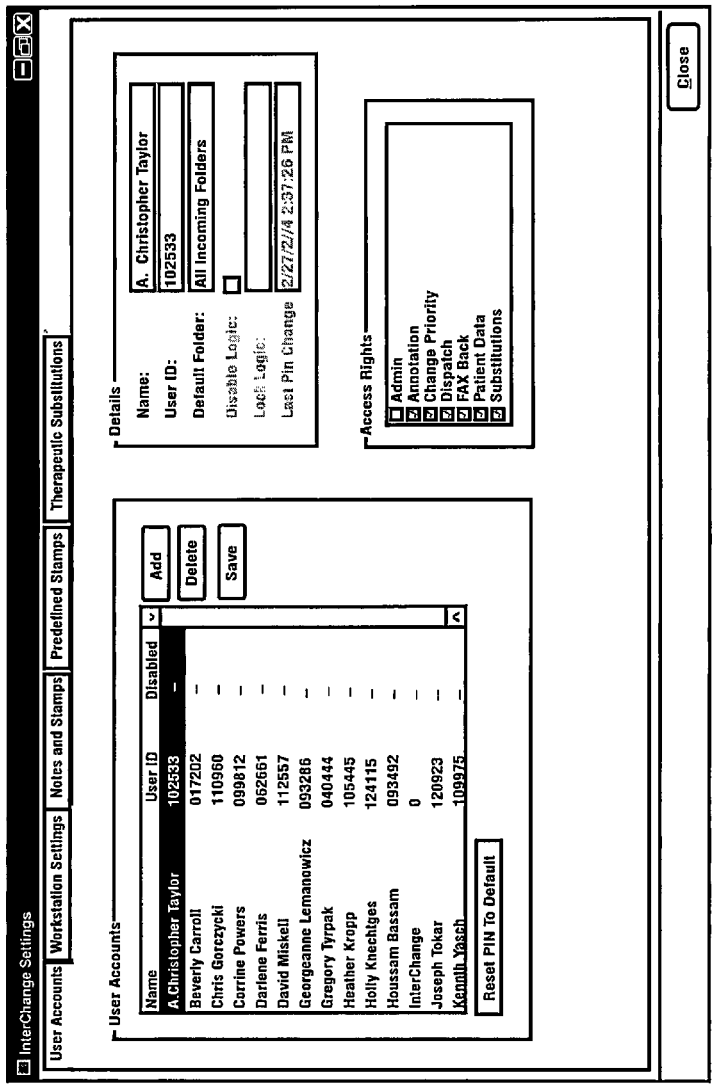
FIG. 19 is a screen output associated with setting up user accounts in an exemplary system.

As represented in FIG. 19 an administrator can set numerous parameters for a given authorized user. These features and functions include the authorized user's name and user ID. As previously discussed this user ID is used to sign on the pharmacist work station may be input manually or via a card or other article. Also in the exemplary embodiment, when first established user accounts have a default PIN which the user is provided and which can be used for the first user login. However the user is prompted on that first login to set their own unique PIN which is unknown to anyone but them. Further in accordance with parameters established through the programming of the system the user may be required to change their PIN periodically.

Other options which can be set through the user account configuration window shown in FIG. 19 include the setting of a default folder. This is a category or a "folder" that the user will review after logging in. The default folder selection is generally configured as a drop-down list of various options. Most often this is set to all incoming faxes, but it may be set in other situations to other categories of items such as physician orders coming from particular nursing stations or items that have been placed on hold.

Other options that can be set by an administrator through the user account window include the disable login function. Disable login when checked, disables the user account. Outputs are also provided through the exemplary user account window indicating the last login for the user as well as the last time that the particular user has changed their PIN. User details are selected by highlighting a name in the left-hand portion of the window. Further as indicated in FIG. 19 there is also a selection that enables the administrator to reset the PIN of a particular user to a default value. This may be done, for example, if a user is concerned that their PIN data has been compromised and they wish to set a new PIN the user may do so on the next login after the existing PIN has been cleared.

As represented in FIG. 19 users may be selectively provided with certain access rights. The particular access rights provided to a particular user are indicated for the user whose name is highlighted in the left-hand portion of FIG. 19. Rights can be provided to a user by inputs by an administrator that result in checkmarks in boxes. These rights may include administrative rights that allow the particular user to have access to all the administrative functions. This is generally provided only to persons in a supervisory position. Other rights include annotation rights which enable a user to make and save annotations on electronic representations of orders. A change priority selection enables a user to raise a priority of a particular medication order from normal to stat, as well as to lower a priority from stat to normal.

The dispatch access right enables the designated user to dispatch an image. The fax back authority allows a user to send an image either back to the originating fax machine, to a predefined department fax machine or to other fax machines. Selecting the patient data access right allows a user to manually add data to patient data fields. Selection of the substitution right enables the authorized user to make a therapeutic substitution. Of course these rights are exemplary and in other embodiments other or different access rights may be provided.

Figure 20:
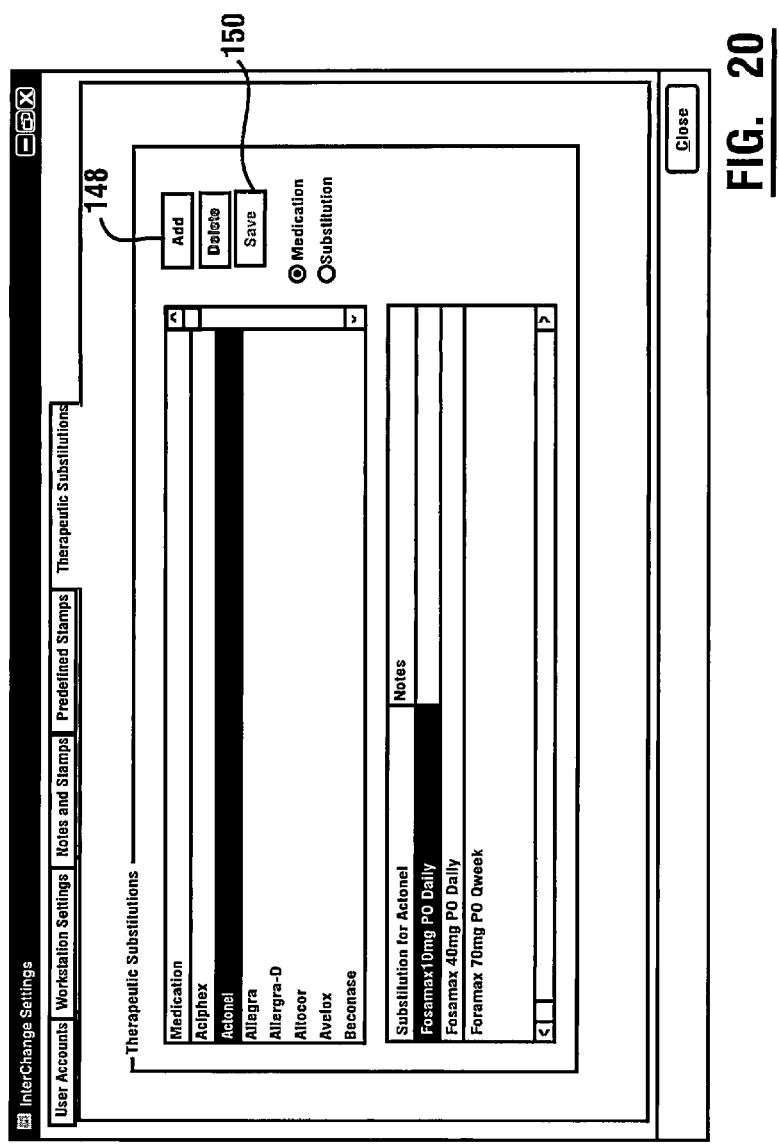
FIG. 20 is an exemplary output screen associated with setting up therapeutic substitutions that may be allowed in an exemplary system.

Certain of the access rights have associated menus and other functionality that is established through the programming of the pharmacist work station or interchange fax station. One of these as indicated by the tabs in the administrative menu is the therapeutic substitution capability. In the exemplary embodiment, selection of the therapeutic substitution folder by an administrator causes the output of the therapeutic substitution screen shown in FIG. 20. There are two portions or windows associated with the screen. The upper portion contains the medication for which a substitution can be made. When a particular medication is highlighted in the upper window, the lower window shows the nature of the approved substitutions. In exemplary embodiments a medication may have more than one approved therapeutic substitution. These substitutions may be, for example, another medication, a medication dose, administration frequency, administration route or other substitution criteria. As previously discussed, approved therapeutic substitutions may be set in accordance with hospital policy or some other medical policy. For example, a hospital pharmacy can have medical substitutions (e.g., medicines, devices) set in accordance with authorized substitution tables and rules located in a data store that is accessible by the pharmacist work station.

In the exemplary embodiment an administrator may add a new medication to the therapeutic substitution by selecting the add button 148. After selecting the add button the desired medication name is input and selecting the save button 150 saves the particular medication. The associated substitution for this medication is added by clicking into the lower window shown in FIG. 20 and selecting "yes" when prompted to add a new substitution for the medication selected in the upper window. This can alternatively be accomplished by selecting the substitution radio button on the right-hand side of the screen.

An authorized administrator may edit medications and their substitutions by placing the mouse pointer into the text to be changed, modifying the existing text and selecting the save button 150. In the exemplary embodiment, if an administrator makes a change and attempts to change another medication or substitution or to close the window without saving, the pharmacist work station is operative to cause a prompt to appear asking the user if they want to save the changes. Selecting a "yes" button that appears saves the changes. Pressing a "no" button discards the changes. Of course this interface approach is exemplary and in other embodiments other approaches may be used.

Figure 21:
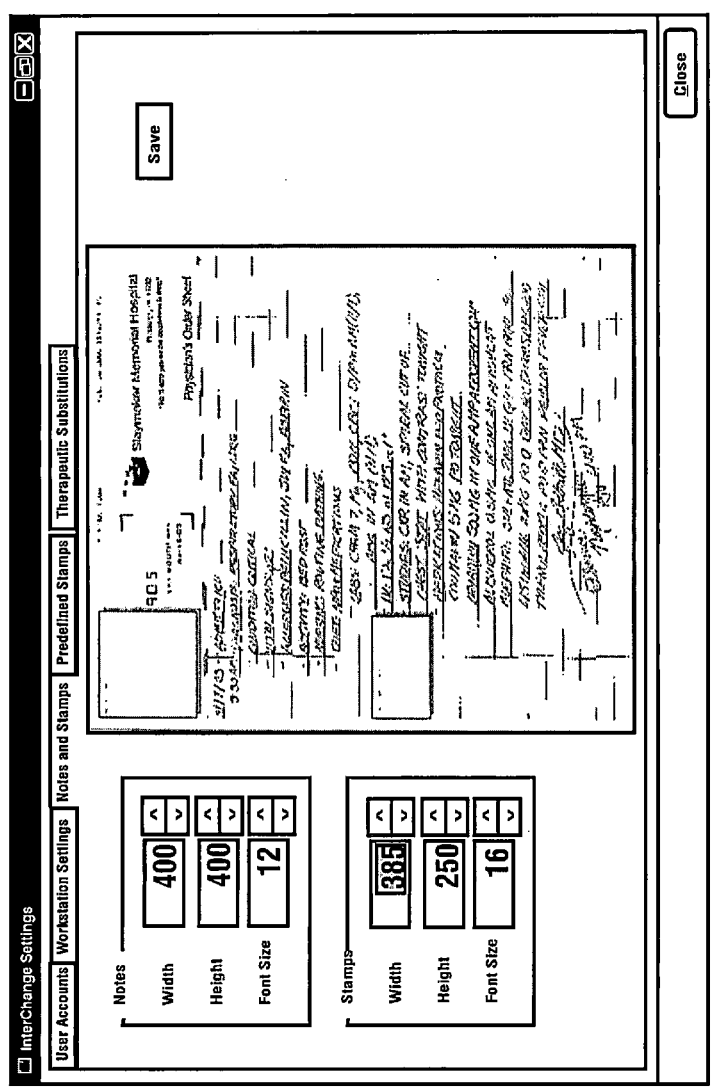
FIG. 21 is an exemplary output screen for configuring the size of notes and stamps that are applied to physician order images.

FIG. 21 shows the setup that an administrator may use associated with the note and stamps configuration folder that is accessible by an administrator. The notes and stamp configuration function allow a default width and height, as well as text font size to be used in conjunction with applying notes and stamps to electronic fax images. Electronic representations of note and stamp boxes are displayed over a sample fax image to help the user visualize the size of these boxes and their fonts. This is represented in FIG. 21.

An administrator may input values into the width, height or font size fields or up and down arrows may be selected by a user to make desired size adjustments to the default size for notes and stamps. In the exemplary embodiment the ability of the administrator to set the default size of the notes and stamps facilitates placing such markings in a suitable size in the electronic images so as to facilitate the readability of both the original fax image as well as the markings applied thereto by the pharmacist.

Another folder that may be selected by an administrator from the administrative menu is the predefined stamp settings. Selecting this folder results in the administrator being presented with the predefined stamp output screen shown in FIG. 22. As previously discussed stamps are made to include predefined text which is frequently used by a pharmacist to indicate some aspect of the physician order. For example, stamps frequently used by a pharmacist may indicate a need for a particular type of clarification associated with the physician order. Some exemplary stamp text content is represented in FIG. 22.

Figure 22:
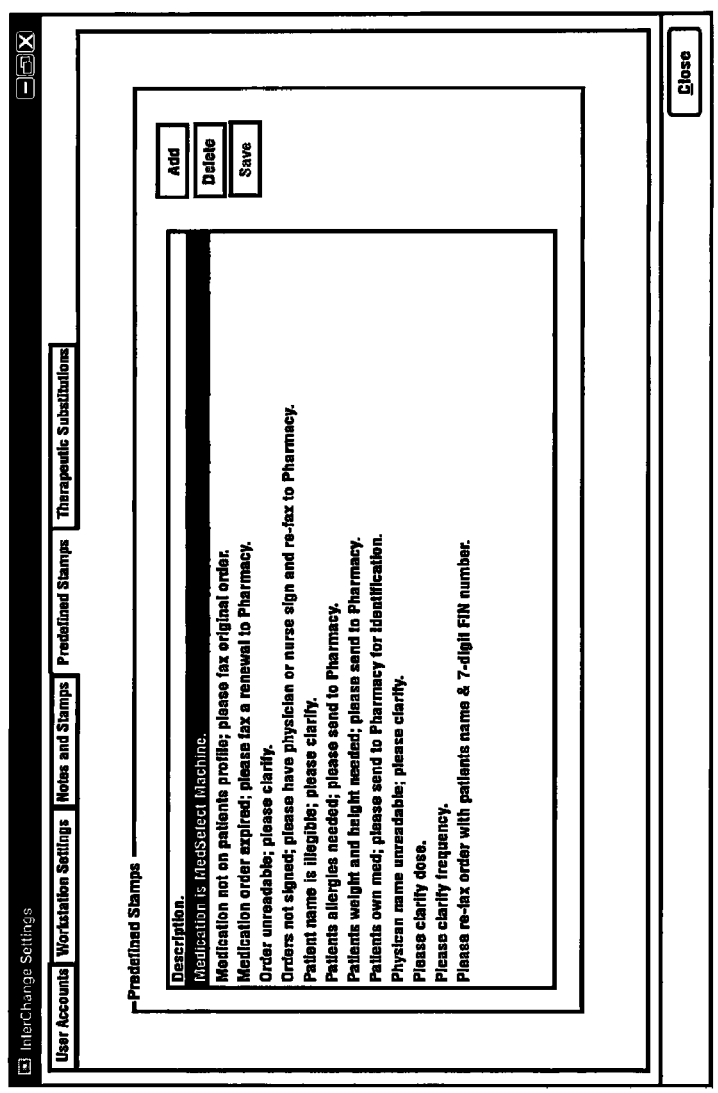
FIG. 22 is an exemplary screen for inputting predefined text to be included in stamps applied by pharmacists on physician order data.

In exemplary embodiments, stamps may be created for storage in a data store associated with the pharmacist work stations by selecting the "add" button shown in FIG. 22. The administrator then enters the desired text and selects the save button. In an exemplary embodiment, stamps can also be edited by placing the mouse pointer into the text to be changed and making the modifications. Once the modifications are made the user may select the save button. Provisions are also made for reminding a user who has inserted a changed stamp text to save the text as changed if they have not selected the "save" button before attempting to close the window. Of course these approaches are exemplary and in other embodiments other approaches may be used.

It should be understood that in some exemplary embodiments the pharmacist work station or other computer may be programmed so as to selectively provide the administrative functions to various persons. For example, in some embodiments the system may be configured so as to strictly limit access to administration functions to particular individuals. In other embodiments, systems may be configured to allow authorized users who do not have formal administrative access to nonetheless access certain aspects of the system such as to set note and stamp sizes or to create customized stamps related to the particular type of physician orders that they may be handling.

In operation of an exemplary embodiment of the system, a physician writes an order for one or more medications that a patient is to receive. This may include the completion of a form or other document which sets forth information about the patient, their condition, diagnosis, vital signs and other information that the pharmacist may be required to know. FIG. 3 shows an example of an order with some of the information that may be normally included on such a form. When the physician or his designee has completed the form, the physician will generally sign the form and provide it to a nurse. It should be understood that although in the exemplary embodiment the use of a paper form is discussed, in alternative embodiments physician orders may be electronically created and signed electronically such as with digital signatures, signature representations, facsimiles, or other suitable indicia of authenticity which shows that the physician responsible has approved the particular order.

In the exemplary embodiment, once a physician order has been completed and signed, a nurse will place the physician order in a fax machine located at the nursing station. The nurse has the option to send the fax either to the high priority phone number or extension number for receiving stat faxes, or to another number which is designated for normal priority orders. In exemplary embodiments the fax machine used will generally be preprogrammed with these numbers so as to facilitate the nurse sending the fax rapidly to the appropriate number.

It should be understood that in alternative embodiments other methods of capturing and dispatching image data may be used. These may include, for example, scanning the particular physician order document at the nurse's station using a scanner connected to a computer or other suitable device so as to provide the document in a format other than a fax format. This may also include adding the electronic representation to a database that is accessible by the computers in the pharmacy rather than specifically dispatching the particular image to a particular phone number. Of course when physician orders are created electronically, other approaches consistent with the manner of inputting the physician order may be used.

In the exemplary embodiment, after the nurse has dispatched the fax to the pharmacy the electronic image represented by the fax is received by the computer which makes up the interchange fax station 28 in the pharmacy. The computers are operative to place the order in queue in accordance with the priority assigned to the order and the time of receipt.

Pharmacists working at pharmacist work stations are automatically presented with the next fax in the queue. This is done in accordance with the administrative settings set for the particular system. Generally however the system is configured so that the faxes having the highest priority are presented first. These would include the stat orders or normal orders that have been waiting the longest. Of course as previously discussed, orders that have been placed on hold will automatically be sent to the top of the queue through operation of the computer once the hold period has expired.

As previously discussed in an exemplary embodiment and in accordance with the administrative settings, the image of the medication order can be automatically zoomed to the defined quadrant so as to readily show to the pharmacist information such as the patient name and ID number. In response to reviewing this information the pharmacist will then use input devices to call up the corresponding data for the patient through the connected pharmacy order system. As previously discussed in the exemplary embodiment, this is done through the input devices such as the mouse and keyboard of the pharmacist work station. Further in an exemplary embodiment the outputs produced by the pharmacy order system will be generated an output through the second screen attached to the pharmacist work station.

The pharmacist will then review the physician order for medications and will take the appropriate action. This may include putting the information into the pharmacy order system. It may also include providing appropriate annotations on the electronic image of the order, faxing the annotated image back to the originating fax station or to another source, placing the order on hold, discarding the order or taking other appropriate action. Upon the pharmacist completing the order, placing the order on hold, or discarding the order, the image data including the annotation data is stored to the database in association with the interchange fax station. The pharmacist work station and interchange fax station then operate in accordance with their programming to present the next physician order to the pharmacist for handling.

It should be understood that in exemplary embodiments provision may be made for recovering and storing physician order data in its original form without modification as well as recovery of the order with annotations. This may enable users to selectively produce the original order or the annotated order as desired. In addition, in some embodiments, provision may be made for assuring that the original physician order and/or annotated physician order version are verifiable as not having been changed subsequent to entry of the order into the pharmacy system. This may include, for example, having the interchange fax station, pharmacist work station, or both applying appropriate digital watermarks, verification codes, authentication indicator, or other suitable means that helps to assure that the particular data stored is accurate and original. Of course these approaches are exemplary and in other embodiments other approaches may be used.

Systems operated in hospitals and other medical facilities may be used to facilitate the delivery and tracking of medication orders that are prepared by pharmacists and included in the pharmacy order system. Exemplary devices, systems and methods for such systems are shown in the following patents and applications which are owned by the assignee of the present invention and the disclosures of which are incorporated herein by reference. These patents include U.S. Pat. Nos. 5,404,384; 5,533,079; 5,790,409; 5,848,593; 5,912,818; 5,957,372; 5,961,036; 5,971,593; 5,993,046; 6,019,249; 6,073,834; 6,108,588; 6,112,502; 6,141,942; 6,163,737; 6,470,234; and 6,658,322. In addition the disclosures of the following U.S. Patent Applications are incorporated herein by reference: Ser. Nos. 09/014,076; 09/086,857; 09/288,685; 09/384,650; 09/428,035; 09/428,036; 09/849,625; and 09/921,014.

As previously discussed in some embodiments a pharmacist operating the pharmacist work station reviews the faxed image or other generated image of a medication order of the screen output on a display screen. In response to reviewing this electronic representation of the medication order, which is also alternatively referred to herein as a prescription, the pharmacist can then note the name of the patient or other information about the patient for which one or more medications has been prescribed. The pharmacist may then operate the pharmacist work station to provide one or more inputs which correspond to the patient. This then causes the pharmacist's work station to communicate with the pharmacy system and is operative to cause one or more computers therein to provide on the other display screen of the pharmacist's work station an output which includes the information that the pharmacy system has related to the particular patient. This information may include for example numerous items of information related to the patient. Items of information that may be output through the display screen of the pharmacy system will typically include the patient's name, the visit number, master reload number associated with the patient (MRN), the patient's date of birth, the patient's gender, the patient's social security number, the patient's primary physician and other information.

In some embodiments it is sufficient to copy the information output by the pharmacy system graphically through operation of the at least one computer of the medication order system so that this information may be stored in a database of the medication order system in correlated relation with the data that corresponds to the image of the medication order. However, the copied graphical data can be difficult to search in a database unless there is also stored related forms of searchable data. Such searchable data facilitates recovery of the data related to the medication order as well as the data corresponding to the associated image. As a result in some embodiments the pharmacist may manually input through the pharmacist work station the data shown through the screen output produced by the pharmacy system. This may include for example the patient name, date of birth, gender, visit number, MRN and the like. This data can then be populated in a data record that includes data pointing to the file which corresponds to an image of the medication order as well as any virtual markings associated with the order, and stored in a database associated with one or more computers operatively connected to the medication order system. This approach enables the data corresponding to the image and data related to the medication order to be identified and recovered more quickly by searching the database through operation of a computer operatively connected therewith. For example in response to user inputs through input devices connected to the pharmacy work station or other connected computers, records may be searched by the patient's name or other stored parameters, and the correlated data corresponding to an image of the medication order, may be output, viewed and analyzed. As can be appreciated this can be accomplished by storing the data in a database associated with the interchange fax station, the pharmacist work station or one or more other computers operatively connected with the medication order system.

Advantages may be obtained by automatically transferring data that can be viewed from the pharmacy system concerning the patient, to the medication order system. This can be done for example by using character recognition software to analyze the data which causes characters to be output from the pharmacy order system to produce the display screen, using character recognition software. Such character recognition software analyzes the nature of the outputs which comprise characters included in the screen displays and attempts to determine corresponding values of such characters. This can be done for example by analyzing the signals which are output from the pharmacist's work station to the display screen, which signals produce the characters which are presented thereon. By having the character recognition software analyze and determine values which correspond to what is being output on the screen, such values can then be communicated electronically and stored in records associated with the medication order system. These values can be used to populate records in one or more data stores of the medication order system that are stored in correlated relation with the data which corresponds to medication order images. This approach can avoid the need for the pharmacist to manually key in the data to be stored in correlated relation with the images in the medication order system.

There are some potential drawbacks associated with the approach of using character recognition software for some systems. One of the drawbacks associated with this approach is that some character recognition software may be only about 90 percent accurate. Such low accuracy is not sufficient for a medical system which must be nearly 100 percent accurate. As a result using character recognition software may result in errors and/or the need for the pharmacist to do an undesirable amount of manual input to correct errors introduced by the character recognition software.

Another potential drawback associated with using character recognition software is the generally substantial cost associated with licensing and maintaining copies of such software. Additionally character recognition software that is designed to be used with numerous types of characters can also consume system resources which slows system performance.

Some exemplary forms of systems may benefit by providing features that determine characters output on a display of the pharmacist work station responsive to operation of a pharmacy system, and then automatically provide this data in data streams to computers operatively connected to the medication order system. Such an exemplary system may take advantage of the fact that a given pharmacy system would generally output characters in only one particular font. Characters included in this font may each be represented as a set of values which correspond to bitmaps which can be used for purposes of comparison of unknown characters so as to identify the type of characters. Identified characters can then be represented by such values in a data stream which is delivered to the medication order system to provide the data which is stored in records correlated with images of prescriptions. Further the nature of the data represented by output characters can be determined through the operation of a computer, based on the area or zone from the output record from which the data was taken. Thus for example it may be known that in the particular zone of the output produced by a pharmacy system, the patient name is presented. By having the system indicate that the data stream was based on outputs in this particular zone, the at least one computer is operative to treat the data stream from that zone as the patient's name data in a data record that is stored in the medication order system. Similar approaches may be taken with regard to data streams generated from other zones. Of course these approaches are exemplary.

Figure 23:
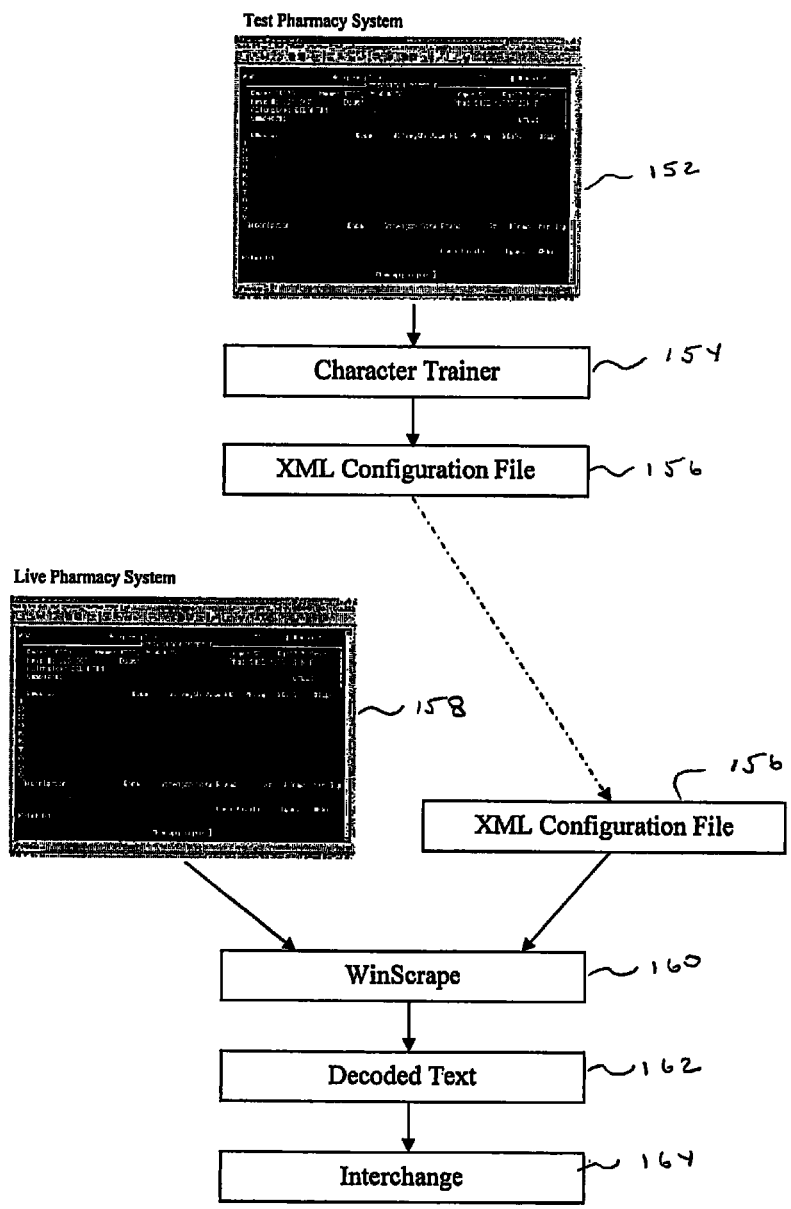
FIG. 23 is a schematic view showing the processes by which an exemplary embodiment can be configured to automatically capture data from a pharmacy system for storage in conjunction with images of medication orders in a medication order system.

FIG. 23 shows a schematic representation of a method by which the pharmacist's work station and/or other computers operatively connected to a medication order system can be programmed to automatically identify and deliver patient related data from the pharmacy system to records of a medication order system. The exemplary system uses one or more test screens 152 that are output on a display of the pharmacist work station. These test screens 152 are produced by the computers operatively connected with the pharmacy system and include characters that normally need to be identified in outputs from the pharmacy system, and then stored as data fields in records. In at least one database of the medication order system as represented schematically by process 154, the types of data output in displays from the pharmacy system are input as part of the configuration process. In addition to the types of data, the areas or zones where the corresponding data is output on a screen are defined by inputs to the pharmacist's work station or other computer. Further the characters which are output from displays of the pharmacy system are defined as sets of values which correspond to bitmaps of the characters themselves.

In process 154 a user configuring the system provides other data such as whether the background of the characters is dark or light, that is used by the computer in analyzing the data to identify pixels which are part of a character from background data. In addition in the exemplary embodiment other data is input such as whether the characters have serifs, spaces between characters and threshold values which delineate whether a pixel is part of a character or part of the background. Further in the exemplary embodiment filter data is also input. Filter data is used in the manner later discussed to determine the type of data included in a particular zone or area of a screen output when two different types of data may be included therein.

In the exemplary embodiment the result of process 154 is to produce at least one markup language document schematically represented 156. The markup language document comprises an XML configuration file which provides definitions concerning the types of data found in a pharmacy screen output, where the data is found and how to identify the characters which make up the data.

Once the XML configuration file 156 has been produced, it is used in one or more computers operatively connected to the pharmacist's work station and the medication order system to enable such computers to determine data included in different zones of outputs from the pharmacy system. As schematically represented in FIG. 23 an output screen from the pharmacy system 158 is produced on a display screen operatively connected to the pharmacist work station. Display screen 158 includes visual representations which include data that is required to be included in records that are correlated with the data that represents the visual image of the prescription that has been submitted to the system for the particular patient to which the screen 158 pertains. Using the schema of the markup language document, the pharmacist system work station operates to capture data from the various identified zones within the screen output, determines the characters included in these various zones and provides the data to the medication order system in a usable form for purposes of inclusion in the records thereof.

This is accomplished in an exemplary embodiment by analyzing the signals which are presented by the pharmacist work station to the display screen so as to produce the screen outputs. These signals are analyzed by screen scraper software schematically represented 160. The screen scraper software captures data corresponding to pixels which make up the display that is output through the screen. This data is then analyzed and decoded in accordance with the schema of the XML configuration file 156 through a process indicated 162. The process 162 then produces data strings which correspond to the desired data related to the patient to which the medication order pertains. This data which is resolved from the screen data based on the information included when the XML configuration file 156, is then output to the interchange software 164. The interchange software of the exemplary embodiment operates to place the data strings in the appropriate records which are correlated with the data that corresponds to a visual representation of the particular medication order. This information is then stored in one or more databases in operative connection with the medication order system. The records which contain this data can then be searched through operation of one or more connected computers so as to recover the data and the corresponding visual representation of the medication order. Of course as previously discussed, this visual representation will also generally include the virtual markings that have been placed on the medication order in connection with its processing.

An aspect of an exemplary form of the system for transferring data between the pharmacy order system and the medication order system is explained with reference to FIGS. 26 through 29. The signals which produce the display outputs corresponding to information stored in the pharmacy order system concerning a patient, is made up of pixels. Each pixel contains red, green and blue values in the case of the color image. For purposes of the exemplary embodiment these color images need to be converted through operation of a program in a pharmacist's work station to a black and white image. This is accomplished in operation of the exemplary embodiment by calculating a number based on the red, green and blue values of each pixel. This calculated number is then compared to a user programmable gray threshold value which determines whether the pixel should be treated as being black or white for purposes of the analysis that will be conducted to identify the character. As previously discussed the gray threshold value is programmed by a user based on the particular system to assure that pixels which comprise characters are properly delineated from pixels which represent the background of the particular system. Also as previously discussed, values which indicate whether the background on which characters are presented is dark or light is also a programmable value input by the user and is used to delineate pixels which correspond to characters and background pixels.

Of course as can be appreciated, in systems which provide monochrome outputs the routines used to delineate between the components of signals to the displays comprise characters and those that make up background, does not require the calculation based on the red, green and blue values for a given pixel.

In an exemplary embodiment the signals which cause the output of a screen are analyzed in identified zones in a manner which will be later discussed. The characters are scanned through operation of the screen scraper software which can be considered for purposes of human understanding as essentially scraping a vertical bar horizontally across columns of the output pixels which make up the characters. This scraping of a vertical bar across the character "a" is graphically represented in FIG. 26. The vertical bar can be thought of as moving left to right across the character. Each of the pixels included in each vertical column is analyzed through operation of the software based on its red, green and blue values, and converted to either a black or white pixel which is interpreted as either a 0 or a 1, respectively for each pixel in the column. These 0 and 1 values or bits are then combined to form an integer value which represents that column of bits. In this way each character of interest which is presented through outputs from the pharmacy system can be identified as a series or set of values.

In an exemplary embodiment the WinScrape Active X control coded using VB6 is operated as the screen scraper software. This provides the integer size of 32 bits which enables a character height of 31 pixels in the exemplary embodiment, as a sign bit is not used. In alternative embodiments 'int64' type VB.Net consists of 64 bits including the bit size. Therefore in an embodiment that uses this software application the column height is 63 pixels as the bit sign is not used.

In an exemplary embodiment the least significant bit in each column value (bit 0) represents the top of the image and increasing bit positions corresponds to downward disposed positions in the column. This follows the pixel convention that is used in Microsoft Windows® where the upper left hand corner of the screen is origin location 0,0 with X values increasing when moving to the right and Y values increasing when moving downward relative to the origin.

Thus for example as shown in FIG. 28, the columns of pixels which make up the letter "t," as a series or a set of bits having a 0 value representing the bits which comprise part of the character, and the bits having the value of 1 corresponding to the background. Thus for example, the bits shown in FIG. 28 corresponds to the highlighted "t" in FIG. 27. As can be appreciated from FIG. 28 the bit values which make up the letter can be represented by the hexadecimal values as shown. FIG. 29 shows a similar set of hexadecimal values and the corresponding bits which represent the letter "m." As can be appreciated this approach can be used for a wide variety of letters, numbers and other values which may be included in the screen outputs. For purposes of this disclosure all such letters, values and other symbols included in screen outputs shall be referred to as characters.

Figure 24:
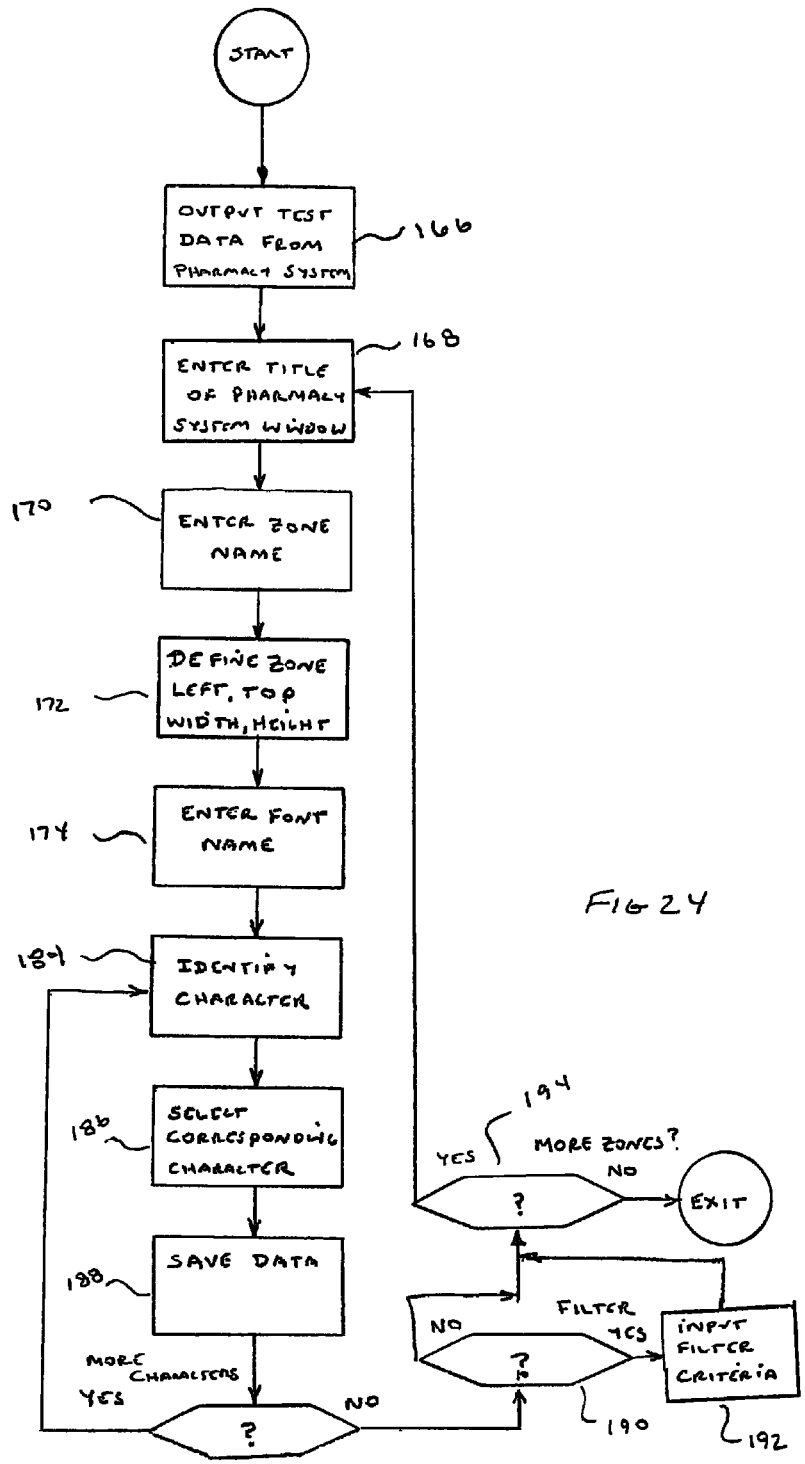
FIG. 24 is a schematic view of the process for developing the data necessary to produce an interface between the pharmacy system and the medication order system represented in FIG. 23.

FIG. 24 represents part of the process 154 that is used in the set up of the system to produce the XML configuration file 156, which is the markup language document that is used in system operation for character identification and recognition and which enables the interfacing of the pharmacy system to the medication order system. As represented from a step 166 in FIG. 24 an output is produced from the pharmacy order system. In the exemplary embodiment this is a test output that preferably includes all of the characters that the system will need to identify for purposes of analyzing the character data that is to be included in the medication order system. Further in the exemplary embodiment this test output also hopefully includes all of the areas or zones from which data is to be captured and analyzed from patient related outputs from the pharmacy order system.

In the exemplary embodiment the process for configuration and developing the configuration file first requires that the user preparing the configuration input a title to be associated with the pharmacy system window that will be analyzed. This is represented in a step 168. In the exemplary embodiment this is done by a user operating the pharmacist work station and the identifying value is provided to at least one input device connected with the work station. Such an input device may include in exemplary embodiments, a keyboard and/or mouse which are operated in conjunction with a Windows interface to identify the particular type of value being input and the name of the pharmacy system screen or window involved. This input value is also included through operation of the software that operates in the pharmacist work station, in the XML configuration file. FIG. 30 which shows an exemplary XML configuration file which includes this input value as the "window title value."

In a next step 170 represented in FIG. 24 a user identifies and enters a name to be associated with an area or zone of the output from the pharmacy system. In the exemplary embodiment this zone name value corresponds to the particular type of data that is included in that particular zone. In the exemplary embodiment zones are identified for patient name, visit number, MRN, date of birth and gender. Of course in other embodiments other or additional zones and zone names may be used. For purposes of this example it will be presumed that the zone being identified in step 170 is the zone in the pharmacy system output that includes the patient name. This also corresponds to the "patient name" zone shown in the exemplary XML schema of FIG. 30.

Once a zone name has been entered the user then operates the pharmacist work station in accordance with its programming to define the area of the zone as represented in step 172 in FIG. 24. In this exemplary embodiment as further shown in connection with FIG. 30, a zone is defined by including left, top, width and height values. These are identified in the exemplary embodiment through pixel coordinates. Of course in other embodiments other approaches may be used.

In the exemplary embodiment the software operating in the pharmacist work station to configure the system then executes a step 174 in which a user is prompted to enter a font name. This font name identifies the particular type of font that is presented in the zone that they have specified. This font name may correspond to an established name for a particular font or alternatively may be a name that has been fancifully developed by the person inputting the data. The importance of the font identifier name is primarily so that other zones which present information in the same font are identified by the same font name. If other zones that are included in the particular pharmacy output use a different type of font, those must be likewise consistently identified through input of the different font name. The value assigned as the "font name" in the example represented in FIG. 30 is Arial, which of course is merely exemplary.

In the exemplary system the test output provided by the display of the pharmacist work station is then used to identify particular characters to the system that can appear in the output from the pharmacist work station in the particular identified zone. In the exemplary embodiment the pharmacist work station operates in accordance with its programming to reproduce on the display screen used for the medication order system a duplicate of the identified zone. On this duplicate of the identified area is reproduced on the other screen in area 176 of a character trainer screen 178 shown in FIG. 25. Trainer screen 178 is produced through operation of software operating in the pharmacist work station or other computers in the medication order system in operative connection therewith.

The characters produced in area 176 are produced by the screen scraper operating in the computer to capture the signals producing outputs in the zone of interest in the output produced by the pharmacy system. These signals which produce the output area are scraped to duplicate the output characters in the area 176.

The red, green and blue pixel values associated with each of the pixels which make up each of the characters are then combined through operation of a computer in the manner later discussed to produce a value. This value is then compared through operation of the computer to a black and white threshold value programmed into the system to produce the equivalent black and white characters. This black and white threshold value is shown in the trainer screen 178 and is indicated by the value "127." Based on the comparison to this threshold value characters are then reproduced in a black and white format in an area 180 of the trainer screen.

It should be understood that as indicated by the arrows in the trainer screen adjacent to the black and white threshold value, that in the exemplary embodiment the value can be adjusted. Thus if the particular value does not produce an accurate black and white reproduction of the characters, the value may be adjusted responsive to user inputs, up or down until an accurate black and white. This threshold value is referred to as a "gray threshold" value and is included as a value associated with the particular identified font in the XML schema as represented in FIG. 30. Of course in the exemplary schema shown in FIG. 30 the gray threshold value is set at 131. Of course these values are merely exemplary.

In the exemplary embodiment of the system training scheme, the user is also prompted to indicate whether the particular screen output is of dark characters on a light background or a light characters on a dark background. These are indicated by the dark text and light text buttons in the training screen 178. The background data is also represented in the XML schema at FIG. 30 by the "dark text on light" data or value included therein.

Also required to be represented in inputs by a user responsive to the character training screen is character separation data. This character separation data is the minimum number of pixel columns per space between characters. This is indicated as "5" in the exemplary training screen 178, and as indicated by the arrows is subject to adjustment responsive to user inputs. The representative value included is "5" which is the indicated minimum number of background pixel columns between characters for this particular font type. This input value is also included in the exemplary XML schema shown in FIG. 30 as the "min cols per space" data value. This character separation data is used for purposes of assisting the system in determining where characters begin and end as is later discussed.

In the exemplary system the computer software operative in the pharmacist work station which produces the training screen also facilitates the identification of the characters that are output from the pharmacy system as known character values. This enables each character to be represented as a set of values which corresponds to columns of bits, the bits in which columns correspond to the shape of the character. By knowing what character's shape corresponds to a known value, the exemplary system is then enabled to have a computer include the values in data fields stored in one more data stores associated with the medication order system. Of course as previously discussed, the records including these data values are then correlated with data which corresponds to an image of a particular medication order.

Figure 25:
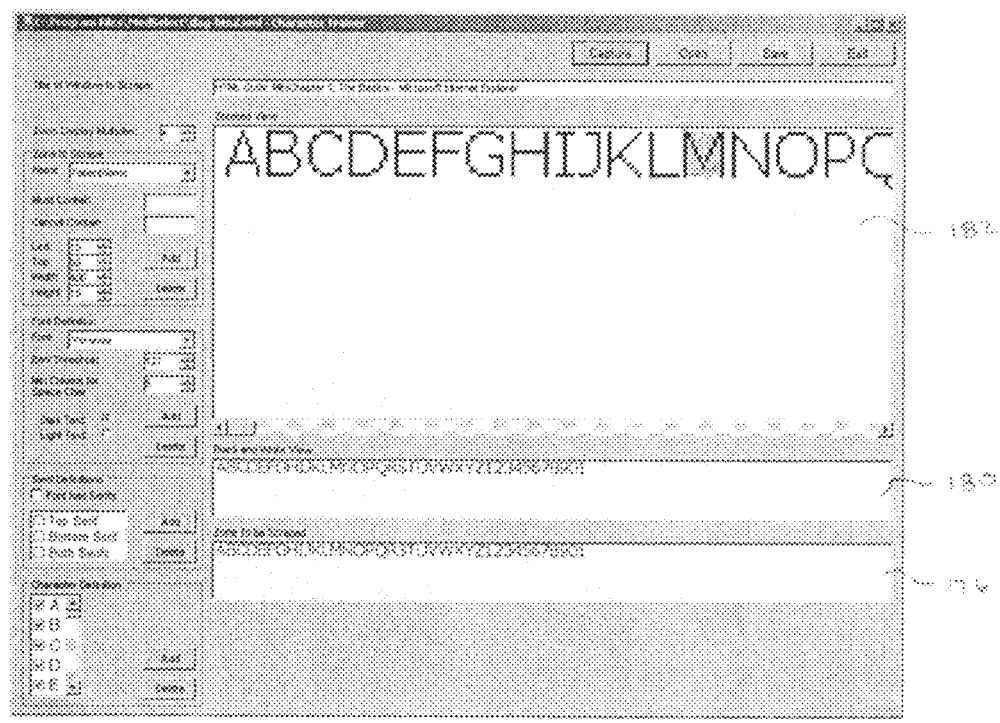
FIG. 25 is an exemplary screen output produced by the medication order system for purposes of configuring the medication order system to interface with a pharmacy system.

In the exemplary embodiment the trainer screen is operative to produce an enlarged or zoomed view of the particular zone and includes the characters represented in 180. This is shown in FIG. 25 by the area 182. In operation of the system the user is then enabled to operate an input device such as a mouse, to highlight the particular character in the string of enlarged characters in area 182. The computer executing the software operates to highlight on the screen the particular character which the user has selected. This is represented in FIG. 24 by a step 184. In response to the selection, the computer operates in accordance with its programming to produce the series of values which in the exemplary embodiment are hexadecimal values which correspond to bits which define the shape of the particular character. These values are then collected through operation of the computer of the pharmacist work station into a set of values which correspond to the character.

To identify the particular character which corresponds to the particular set of values which have been produced, a user provides at least one input in response to training screen 178. In the exemplary embodiment the input causes the computer to place a checkmark or other indicator next to the particular character which is highlighted. This is represented in the step 186 in FIG. 24 and by the inclusion of an indicator in connection with particular letter as represented in the lower left hand corner of training screen 178. When the user has indicated the particular character to which the output character corresponds, the user of the pharmacy work station can then save data which represents the relationship between the known character and the set of values which correspond to the shape of the character by clicking the "add" button included in the training screen 178. This saves the data as indicated in a step 188 in FIG. 24.

The computer in response to saving the data corresponding to the particular character is also operative to include the data related to the character set in the XML schema. For example as shown in FIG. 30 the highlighted character "m" in area 182 at screen 178 shown in FIG. 25, has the "char value" shown in FIG. 30 which is comprised of the corresponding hexadecimal values which are shown. It should be noted that these hexadecimal values correspond to the hexadecimal values in FIG. 29, which when converted to binary and aligned indicate the shape of the letter "m."

As represented in FIG. 24 this process is repeated for all of the characters that may be included in the pharmacy test output for which characters are represented in area 182. As a result, a user wishing to identify additional characters repeats the process. The user identifies a different character represented in area 182, provides inputs to select a corresponding character from the list and then stores in the data by selecting "add" which results in the inclusion of another set of character values corresponding to that particular character in the schema as represented in FIG. 30.

As also represented in FIG. 24, a user is prompted to input values in response to training screen 178 which represent filter data. This is accomplished by providing filter data in the "must contain" or the "cannot contain" fields shown in screen 178. The entry of values as filter data are useful in some embodiments for determining the type of data contained in a particular zone. This feature may be particularly useful in situations in which different types of data to be captured may be written within the same zone of a particular pharmacy system output. Alternatively or in addition this feature may be useful where multiple outputs of a pharmacy system are to be analyzed for purposes of capturing data and the same output area of the different screens includes different types of data.

For example in some systems the data included in a particular area of the screen could be either an MRN or a visit number depending on the data being output from the pharmacy system. Because the MRN data includes a "-" in all cases, this can then be used by the computer to delineate whether the data presented in the zone is an MRN or a visit number. In this exemplary embodiment two separate zone identifiers are created, but both zones comprise the same area of an output screen from the pharmacy system. One zone was indicated in the XML configuration file to correspond to an MRN and the other one a visit number. For the MRN zone the "must have filter" is set to include a "-" symbol and the "cannot have" filter data left blank. For the visit number zone which again is the same area on the screen, the "must have" filter data was left as blank and the "cannot have" filter was set to "-" symbol. Therefore when the data in a particular area is analyzed by the computer and the data includes a "-" symbol, then a character value corresponding to an MRN would be determined by the computer and no value would be determined for the visit number. Likewise if the area was determined as not including a "-" symbol then the computer would resolve no MRN value but would return a value for a visit number. Of course these approaches are exemplary and in other embodiments other approaches may be used.

The setting of filter criteria is represented in a step 190 in FIG. 24. The input of filter values is indicated by a step 192. It should be understood that although the filter data is delineated by two criteria namely "must have" and "cannot have" additional or different filter data may be used in other embodiments.

Also included in the exemplary embodiment of the trainer screen 178, are data input values to indicate whether or not the particular font includes serifs. In the exemplary embodiment shown, the user providing data at the pharmacist work station is asked to indicate whether the particular font includes top serifs, bottom serifs or both. As can be appreciated from FIGS. 31 and 32, the presence of serifs at the top and/or bottom of characters may impact how characters are analyzed. Further in the exemplary embodiment the presence or absence of serifs can be used as values in a configuration file to help determine the nature of particular letters.

In the exemplary embodiment the user provides inputs related to whether the font includes serifs through one or more input devices such as a mouse in operative connection with the pharmacist work station. The values that a user inputs are represented in the XML schema shown in FIG. 30 by the serif values which are included in the schema in association with the particular type of named font. Of course it should be understood that these approaches are exemplary and in other embodiments other approaches may be used.

Returning to the schematic methodology associated with configuring the system shown in FIG. 24, once a user has identified a particular zone in the test pharmacy system output and the shape corresponding to the characters that are included in that particular zone, the user may operate the system to identify additional zones. This is represented in FIG. 24 by a step 194 indicating that the user has additional zones to identify. This is done by selecting the additional zone name from the drop-down menu available in the trainer screen 178, as well as by indicating the pixel coordinates for the corresponding zone as indicated by the values for the left, top, width and height of the newly identified zone. When the zone coordinates are properly selected the user can provide an input by selecting the "add" button and then repeat the process to identify the font and characters in that particular zone. The process is then repeated for all of the zones which contain data to be included in the configuration file for the particular system. As previously discussed, in the exemplary embodiment the system operates to identify data which includes patient name, visit number, MRN, date of birth and gender. Of course in other embodiments other zones and values may be used.

Figure 31:
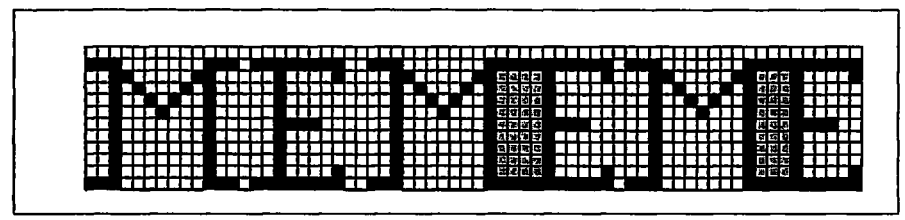
FIG. 31 is an exemplary view of characters that include serifs at both the upper and lower extremities of the characters.
Figure 32:
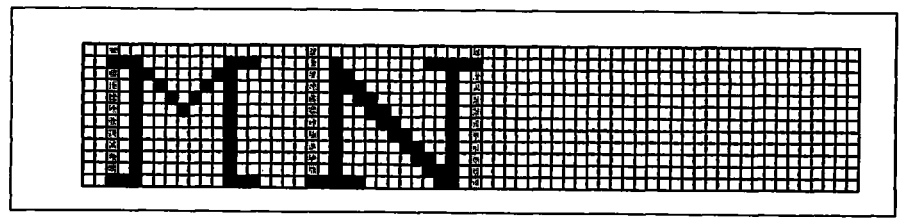
FIG. 32 is a further exemplary view of characters which include serifs.

Once the markup language document has been produced it comprises the XML schema that is used for configuration of the system. This markup language document may be provided to all of the pharmacist work stations in operative connection with the system. In the exemplary embodiment the software operating the pharmacist work station is operative to analyze the characters including serifs in accordance with the configuration data included in the XML document. In some situations when characters are output from a pharmacy order system with serifs, one of the characters may be shortened. For example a capital "M" may end with a serif that is two columns wide and a capital "E" begins with a serif that is two columns wide. When printed as "ME" there may be only three columns of serifs between the two characters rather than an expected four (for example). This is represented in FIG. 31 on the right as shown. In order to accommodate this situation the exemplary software is operative to recognize the columns of pixels that are used to form the serif. This is achieved in an exemplary embodiment because of the information provided in the XML schema concerning whether there are top serifs, bottom serifs or both in connection with the particular characters.

In the exemplary embodiment the computer operates so that when the end of a character is determined but no match is found, it is also noted that the last column that was added was a column of serifs. If this is true then the last exact match to a character is added to the identified character string as usual, but processing is started at the previous column rather than the current. This enables the letters "ME" shown on the right in FIG. 31 to be processed correctly (that is, three serif columns rather than four). If no match can be found after the first three columns have been processed and the computer determines that these columns are all serifs, then it is assumed that the situation of adjacent letters "ME" which has four serifs has been encountered as would be expected. This is represented by the letters shown in the middle in FIG. 31. In this situation the first column of serifs is discarded and the processing continues as normal.

These examples enable a computer of the exemplary embodiment to account for the existence of serifs on letters and to identify letters even in those situations where the serifs result in no separation between the letters. Of course alternative embodiments may perform different forms of analyses depending on the type of characters used and the nature of the serifs included in the letters. Provision may also be made in the programming of the system to include consideration of different character features in addition to or as alternative to serifs depending on the nature of the characters to be analyzed.

As can be appreciated, the exemplary embodiment is operative to provide a highly reliable interface which transfers data which is available in the pharmacy order system to the medication order system. The system also provides such data in a manner that enables the data to be stored in a database in correlated relation with the file corresponding to visual representations of the medication orders. The exemplary embodiment provides a highly reliable method for character recognition as well as a methodology by which a pharmacist can assure that the data that is included in the database of the medication order system appropriately reflects the data from the pharmacy order system. As a result the pharmacist is enabled to determine that the characters that the pharmacist work station or other computer has resolved based on the processes for identifying characters, has operated accurately.

Further in exemplary embodiments the use of the markup language document and particularly an XML schema for purposes of providing the configuration that enables the resolution of character data, can be used effectively for configuring multiple pharmacist work stations and systems. The configuration files can also be readily changed and may include additional or different types of data. It should further be understood that although one markup language document is included in the XML schema of the exemplary embodiment, in other embodiments multiple documents and schemas may be used in connection with the analysis. This may be particularly useful for example, in situations where multiple outputs from pharmacy systems provided through different screens are analyzed for purposes of acquiring different types of data.

In addition although the exemplary embodiment is used in connection with an interface between a pharmacy system and a medication order system, the principles explained may be used in connection with other types of medical or data systems in which it is desirable to interface and transfer data based on data which produces visual outputs provided by one of the systems. Of course it should be understood that although the exemplary system has been described in connection with using visual outputs, some of the principles may be applied to audible or other outputs. Such embodiments may accomplish data transfer such as by using text to speech software. Such text to speech software may be used either to accomplish a direct data transfer from one system to another, or alternatively may produce stored data in response to words spoken by a pharmacist in response to outputs from a system which are then converted to data that is included in records of the system which stores the data in connection with medication order data or other data. Numerous alternatives may be devised by those skilled in the art based on the teachings described herein.

Thus the foregoing exemplary system and method accomplishes one or more of the above stated objectives, eliminates difficulties encountered in the use of prior systems and methods, solves problems and attains one or more useful results.

In the foregoing description certain terms have been used for brevity, clarity and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art to be capable of performing the recited function, and shall not be limited to the structures shown herein or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations, methods and relationships are set forth in the appended claims.

We claim:

1. A method comprising:
   (a) displaying through at least one display screen of a pharmacy workstation, an image of a first prescription received from a medication order system,
      wherein the first prescription is for a first patient from among a plurality of patients for which patient data is stored in a data store of a pharmacy system,
         wherein the pharmacy system is distinct from the medication order system,
      wherein the workstation includes at least one processor,
      wherein the workstation is operable to communicate with the pharmacy system and the medication order system,
   (b) displaying through the at least one display screen, first patient data accessed from a data store of the pharmacy system,
      wherein the first patient data corresponds to the first patient;
   (c) operating the workstation to perform through application of definition data included in at least one schema, computer analysis of the first patient data,
      wherein the definition data defines a plurality of zones corresponding to different screen areas of the first patient data displayed in the at least one display screen,
         wherein a first zone of the plurality of zones corresponds to a first screen area of the first patient data,
            wherein the first screen area includes a name of the first patient,
         wherein at least one other zone of the plurality of zones corresponds to at least one other screen area of the first patient data,
            wherein the at least one other screen area includes at least one of: a record number, first patient gender, a visit number, or a person having a relationship to the first patient;

(d) operating the workstation to automatically resolve first patient text data from the analysis performed in (c),
wherein the first patient text data includes data corresponding to the name of the first patient,
wherein the first patient text data includes data corresponding to at least one of: a record number, first patient gender, a visit number, or a person having a relationship to the first patient; and (e) operating the workstation to cause first patient text data resolved in (d) to be stored in at least one data store of the medication order system, in correlated relation with image data corresponding to the image of the first prescription,
wherein the first patient text data is stored as searchable data in a record corresponding to the first patient,
wherein the correlated relation enables the image of the first prescription to be accessed from the medication order system based at least in part on a search of the name of the first patient;

wherein (a)-(e) are performed without manual input to the workstation of:
the image of the first prescription, or
a record number, first patient gender, a visit number, or a person having a relationship to the first patient.

2. The method according to claim 1 wherein the first patient data is displayed in (b) while the image of the first prescription is displayed in (a).

3. The method according to claim 1 wherein in (c) the at least one schema comprises at least one markup language schema.

4. The method according to claim 1 wherein (c) includes comparing data corresponding to first patient data display signals to data included in at least one XML schema.

5. The method according to claim 1 wherein (c) includes comparing
data corresponding to a configuration of at least one character produced in first patient data display signals, and
an arrangement of ones and zeros corresponding to at least one set of hexadecimal values.

6. The method according to claim 1 and further comprising:
(f) prior to (a), producing the image of the first prescription with a scanning device at a station that is remotely located from the workstation.

7. The method according to claim 1 and further comprising:
(f) prior to (a), producing the image of the first prescription with a scanning device that is remotely located from the workstation;
(g) communicating the image produced in (f) from the scanning device to the workstation;
wherein (a) includes displaying the image communicated in (g).

8. The method according to claim 1 wherein a pharmacy includes the workstation, wherein the workstation includes at least one input device, and further comprising:
(f) prior to (b), providing at least one input through the at least one input device, responsive to visual indicia included in the image displayed in (a),
wherein in (b) the first patient data is displayed responsive to the at least one input provided in (f).

9. The method according to claim 8 and further comprising:

(g) subsequent to (c), providing at least one data request input corresponding to at least some of the first patient text data resolved in (d);
(h) recovering from the at least one data store of the medication order system responsive to the at least one data request input in (g), image data corresponding to the image displayed in (a).

10. The method according to claim 8 wherein in (c) the at least one schema comprises at least one markup language schema, and wherein the first patient data is analyzed through the use of the at least one markup language schema.

11. The method according to claim 10 wherein in (c) the definition data includes data defining a location of the first screen area, wherein the first screen area corresponds to less than the entire area of the at least one display screen.

12. The method according to claim 10 wherein in (b) the definition data comprises a plurality of sets of values, each set corresponding to a respective character,
wherein in (c) the workstation operates to:
analyze signals causing output of at least one character in at least one zone of the plurality of zones, and
compare the signals and the sets of values corresponding to characters;
wherein in (d) the first patient text data is resolved responsive to the comparison.

13. The method according to claim 10 wherein (c) includes the operation of screen scraper software in the at least one processor.

14. The method according to claim 13 wherein the definition data includes filter data, wherein in (d) the at least one processor in accordance with the filter data, resolves at least two different types of patient data responsive to characters included in the plurality of zones.

15. The method according to claim 13 wherein in (b) the at least one processor is operable to compare data corresponding to pixels, and bits comprising binary values included in the sets of values corresponding to characters.

16. The method according to claim 15 wherein the at least one schema includes background data indicating whether the characters are dark on a light background, and wherein in (d) resolved data is determined responsive to the background data.

17. The method according to claim 15 wherein the at least one schema includes serif data indicating whether the characters include serifs, and wherein in (d) resolved data is determined responsive to the serif data.

18. The method according to claim 15 wherein the at least one schema includes threshold data corresponding to a threshold that delineates between characters and background, and wherein in (d) resolved data is determined responsive to the threshold data.

19. The method according to claim 15 wherein the at least one schema includes character separation data corresponding to space which separates characters, and wherein in (d) resolved data is determined responsive to the character separation data.

20. The method according to claim 1 wherein the at least one display screen includes a first display screen and a second display screen, wherein the second display screen is separate from the first display screen,
wherein the workstation includes a first display device and a second display device,
wherein the first display device includes the first display screen,
wherein the second display device includes the second display screen, wherein (a) includes displaying the image through the first display screen, wherein (d) includes displaying the first patient data through the second display screen.

21. A method comprising:
(a) operating at least one processor of a workstation to receive prescription image data from a medication order system,
    wherein the workstation is operable to communicate with a pharmacy system and the medication order system,
        wherein the pharmacy system is distinct from the medication order system,
        wherein the pharmacy system includes patient data on a plurality of patients,
    wherein the prescription image data corresponds to a prescription image of a prescription,
        wherein the prescription is for a first patient from among the plurality of patients,
            wherein the patient data includes first patient data on the first patient,
    wherein the workstation includes at least one display screen device;
(b) subsequent to (a), operating the at least one processor to cause the prescription image to be displayed through the at least one display screen device;
(c) subsequent to (b), operating the at least one processor to access the first patient data from the pharmacy system;
(d) subsequent to (c), operating the at least one processor to cause the first patient data to be displayed through the at least one display screen device,
    wherein the first patient data includes a name of the first patient,
    wherein the first patient data includes at least one of: a medical record number, first patient gender, a visit number, or a person having a relationship to the first patient;
(e) operating the at least one processor to automatically capture through application of definition data included in at least one schema, data from display zones of the first patient data displayed in (d),
    wherein the definition data defines the display zones,
        wherein the display zones includes a first display zone,
        wherein the display zones include at least one other display zone,
    wherein the definition data associates respective display zones with respective types of patient data,
        wherein the first display zone is associated with patient name,
        wherein the at least one other display zone is associated with at least one of: a medical record number, patient gender, a visit number, or a person having a relationship to a patient;
(f) operating the at least one processor to automatically resolve first patient text data from the data captured in (e),
    wherein the first patient text data includes data corresponding to the name of the first patient,
    wherein the first patient text data includes at least one of: a medical record number, first patient gender, a visit number, or a person having a relationship to the first patient; and
(g) operating the at least one processor to cause the prescription image and the first patient text data resolved in (f) to be stored in correlated relation in the medication order system,
    wherein the first patient text data is stored as searchable data in a record corresponding to the first patient,
        wherein the correlated relation enables the prescription image to be accessed from the medication order system based at least in part on a search of the name of the first patient;
wherein (a) is performed without manual input to the workstation of the prescription image data,
wherein (b) is performed without manual input to the workstation of the prescription image, and
wherein (c)-(d) are performed without manual input to the workstation of a record number, first patient gender, a visit number, or a person having a relationship to the first patient.

22. The method according to claim 21 and further comprising:
(h) prior to (a), producing the at least one markup language schema through operation of the workstation by:
    (h1) providing at least one test screen output through the at least one display screen device; and
    (h2) providing to the workstation, at least one input that defines at least one of the display zones.

23. The method according to claim 22 wherein the at least one schema comprises at least one markup language schema, wherein (h) further includes:
(h3) selecting through at least one input to the workstation, a character included in the test screen output provided in (h1); and
(h4) selecting through at least one input to the workstation, a character identified as corresponding to the character selected in (h3).

24. The method according to claim 23 wherein (h) further comprises:
(h5) responsive to the selection in (h4), generating through operation of the workstation, a plurality of hexadecimal values corresponding to a bit profile of the character selected in (h3), wherein the plurality of hexadecimal values comprise a set.

25. The method according to claim 22 wherein (h) further comprises at least one of:
(h3) inputting background data through the workstation,
    wherein the at least one schema includes the background data,
        wherein the background data indicates whether characters are dark on a light background; or
(h4) inputting threshold data through the workstation,
    wherein the at least one schema includes the threshold data,
        wherein the threshold data corresponds to a threshold that delineates between characters and background.

26. The method according to claim 21 wherein the at least one display screen device includes a first display screen device and a second display screen device, wherein the second display screen device is other than the first display screen device,
    wherein (b) includes operating the at least one processor to cause the prescription image to be displayed through the first display screen device, and
    wherein (d) includes operating the at least one processor to cause the first patient data to be displayed through the second display screen device.

27. A method comprising:
(a) displaying through at least one display screen of a pharmacy workstation, a prescription image corresponding to prescription image data received by the workstation from a station remotely located from the workstation,
   wherein the prescription image data corresponds to a prescription for a first patient from among a plurality of patients for which patient data is stored in a data store of a pharmacy system,
   wherein the workstation includes at least one processor;
(b) operating the pharmacy workstation to receive from a pharmacy system, display output signals that correspond to a first patient file,
   wherein the first patient file is associated with the first patient,
      wherein the first patient file includes a name of the first patient,
         wherein the first patient file includes at least one of: a record number associated with the first patient, gender of the first patient, a visit number associated with the first patient, or a person having a relationship to the first patient;
(c) operating the workstation responsive at least in part to the display output signals received in (b), to display the first patient file through the at least one display screen,
(d) operating the workstation to cause definition data included in at least one schema, to be applied to the display output signals received in (b),
   wherein the definition data includes data defining a plurality of display zones,
      wherein a first display zone corresponds to location of a patient name in a displayed patient file,
      wherein at least one other display zone corresponds to location in a displayed patient file of at least one of: a record number, patient gender, a visit number, or a person having a relationship to the patient;
(e) operating the workstation responsive at least in part to (d), to automatically resolve first patient file text data from the display output signals received in (b),
   wherein the first patient file text data includes data corresponding to the name of the first patient,
   wherein the first patient file text data includes at least one of: a record number associated with the first patient, gender of the first patient, a visit number associated with the first patient, or a person having a relationship to the first patient; and
(f) operating the workstation to cause to be stored in correlated relation in at least one data store of a medication order system, the first patient file text data resolved in (e) and the prescription image data corresponding to the prescription image displayed in (a);
   wherein (a)-(f) are performed without manual input to the workstation of:
      the prescription image,
      the prescription image data,
      the first patient file, or
      the first patient file text data.

28. The method according to claim 27 wherein the at least one schema comprises at least one markup language schema, wherein the definition data is included in the at least one markup language document schema,
   wherein (d) includes analyzing the display output signals through use of the definition data included in the at least one markup language document schema.

29. The method according to claim 27 wherein (d) includes comparing:
   data corresponding to a configuration of at least one character produced in the display output signals, and
   at least one set comprising a plurality of hexadecimal values.

30. The method according to claim 29 wherein in (d) the at least one set of hexadecimal values corresponds to an arrangement of ones and zeros.

31. The method according to claim 27 wherein the at least one display screen includes a first display screen and a second display screen, wherein the second display screen is separate from the first display screen,
   wherein the workstation includes a first display device and a second display device,
      wherein the first display device includes the first display screen,
      wherein the second display device includes the second display screen,
   wherein (a) includes displaying the prescription image through the first display screen,
   wherein (c) includes displaying the first patient file through the second display screen.

32. A method comprising:
(a) operating a pharmacy workstation which includes a first display device comprising a first display screen and a second display device comprising a second display screen, to cause prescription image data corresponding to a prescription for a patient to be displayed on the first display screen,
   wherein the patient is one of a plurality of patients for which respective patient files are stored in a data store,
   wherein the second display device is other than the first display device,
   wherein the workstation includes at least one processor;
(b) operating the workstation to receive display output signals associated with a patient file of the patient,
   wherein the display output signals are operative to cause the second display screen to produce screen outputs corresponding to the patient file;
(c) operating the workstation to cause patient file data corresponding to the display output signals received in (b), to be displayed on the second display screen;
(d) operating the workstation to cause the at least one processor to perform computer-analysis on the display output signals received in (b),
   wherein the display output signals are analyzed by the at least one processor in accordance with definition data included in at least one markup language schema,
      wherein the definition data includes data defining locations of plural zones in the patient file data displayed in (c),
         wherein a first zone of the plural zones includes a patient name,
         wherein a second zone of the plural zones includes at least one of a record number, patient gender, visit number, or name of a person other than the patient;
(e) operating the workstation to cause the at least one processor to automatically resolve from the analysis in (d), character strings from patient data captured in zones in the patient file data,
   wherein a first character string includes the patient name,
   wherein a second character string includes at least one of a record number, patient gender, visit number, or name of a person other than the patient; and
(f) operating the workstation to cause the character strings resolved in (e) to be stored in at least one data store in correlated relation with the prescription image data, wherein the character strings are stored as searchable data in a record corresponding to the patient,
wherein the record enables the prescription image data to be accessed based at least in part on a search of the patient name in the at least one data store;
wherein (a)-(f) are performed without manual input of any of:
the prescription image data,
the patient file data, or
the patient data.

33. The method according to claim 32 wherein (d) includes comparing
data corresponding to a configuration of at least one character produced in the display output signals, and
at least one set comprising a plurality of hexadecimal values.

34. The method according to claim 33 wherein in (d) the at least one set of hexadecimal values corresponds to an arrangement of ones and zeros.

* * * * *